(12) United States Patent
Iglesias et al.

(10) Patent No.: US 7,311,686 B1
(45) Date of Patent: Dec. 25, 2007

(54) MOLDED ORTHOPAEDIC DEVICES

(75) Inventors: Joseph M. Iglesias, Thousand Oaks, CA (US); Tracy E. Grim, Tulsa, OK (US); Stacy Wyatt, Camarillo, CA (US); Steve Pelote, Vista, CA (US); Luis F. Teran, North Hills, CA (US)

(73) Assignee: Ossur hf, Reykjavik (IS)

( * ) Notice: Subject to any disclaimer, the term of this patent is extended or adjusted under 35 U.S.C. 154(b) by 1247 days.

(21) Appl. No.: 09/704,364

(22) Filed: Nov. 2, 2000

Related U.S. Application Data

(63) Continuation-in-part of application No. 09/504,980, filed on Feb. 15, 2000, now abandoned, which is a continuation-in-part of application No. 09/018,318, filed on Feb. 3, 1998, now Pat. No. 6,024,712, which is a continuation-in-part of application No. 08/580,129, filed on Dec. 28, 1995, now Pat. No. 5,713,837.

(51) Int. Cl.
*A61F 5/00* (2006.01)
(52) U.S. Cl. .......................... 602/20; 602/21
(58) Field of Classification Search ................ 602/4–8, 602/20–23; 128/877–879
See application file for complete search history.

(56) References Cited

U.S. PATENT DOCUMENTS

| | | | |
|---|---|---|---|
| 3,298,365 A | 1/1967 | Lewis | |
| 3,863,272 A | 2/1975 | Guille | |
| 4,134,955 A | 1/1979 | Hanrahan, Jr. et al. | |
| 4,193,134 A | 3/1980 | Hanrahan et al. | |
| 4,280,488 A | 7/1981 | Polsky et al. | |
| 4,292,263 A | 9/1981 | Hanrahan et al. | |
| 4,440,158 A | 4/1984 | Shapiro | |
| 4,524,464 A * | 6/1985 | Primiano et al. | ................ 2/16 |
| 4,558,747 A | 12/1985 | Cunningham | |
| 4,666,158 A * | 5/1987 | Moro | .......................... 473/62 |
| 4,724,847 A | 2/1988 | Nelson | |
| 4,805,273 A | 2/1989 | Burke et al. | |
| 4,825,856 A | 5/1989 | Nelson | |

(Continued)

FOREIGN PATENT DOCUMENTS

EP          332899          9/1889

(Continued)

*Primary Examiner*—Michael Brown
(74) *Attorney, Agent, or Firm*—Bacon & Thomas, PLLC

(57) ABSTRACT

The present invention pertains to an orthopedic support having a flexible inner member and an exo-skeleton that is molded directly onto the flexible inner member. One aspect of the invention relates to a wrist support having a thumb spica. The wrist support includes a molded plastic exostructure supplying support for resisting motion of said wrist. An inner fabric support is attached to said molded exostructure for providing cushioning to the wrist area. A separate, attachable thumb spica member is provided for optionally configuring the wrist support to include a thumb spica. Other embodiments include an orthopedic support having an attachable stay; a web bridge that extends across and supports the web of the hand; an adjustable wrist support having an adjustable forearm portion that can accommodate various sizes of forearms; a wrist brace having a space to accommodate the web of the hand; and a support having an interior padding member, with the padding member itself having a support structure molded onto the padding. Another aspect of the invention relates to a method of molding the exo-structure onto a central core that is placed inside a mold.

26 Claims, 20 Drawing Sheets

U.S. PATENT DOCUMENTS

| | | | |
|---|---|---|---|
| 4,854,310 A * | 8/1989 | Lee | 602/21 |
| 5,020,687 A | 6/1991 | Seizert | |
| 5,093,067 A | 3/1992 | Gibson | |
| 5,323,993 A | 6/1994 | Questel et al. | |
| 5,357,659 A | 10/1994 | Ackerman | |
| 5,456,976 A | 10/1995 | LaMarca, II et al. | |
| 5,584,799 A * | 12/1996 | Gray | 602/5 |
| 5,647,150 A | 7/1997 | Romanato et al. | |
| 5,772,620 A * | 6/1998 | Szlema et al. | 602/21 |
| 5,778,449 A * | 7/1998 | Oetting et al. | 2/16 |
| 5,782,784 A * | 7/1998 | Wassermann | 602/21 |
| 6,024,712 A | 2/2000 | Iglesias et al. | |
| 6,196,985 B1 * | 3/2001 | Slautterback | 602/20 |

FOREIGN PATENT DOCUMENTS

| | | |
|---|---|---|
| WO | WO9412334 | 6/1994 |

* cited by examiner

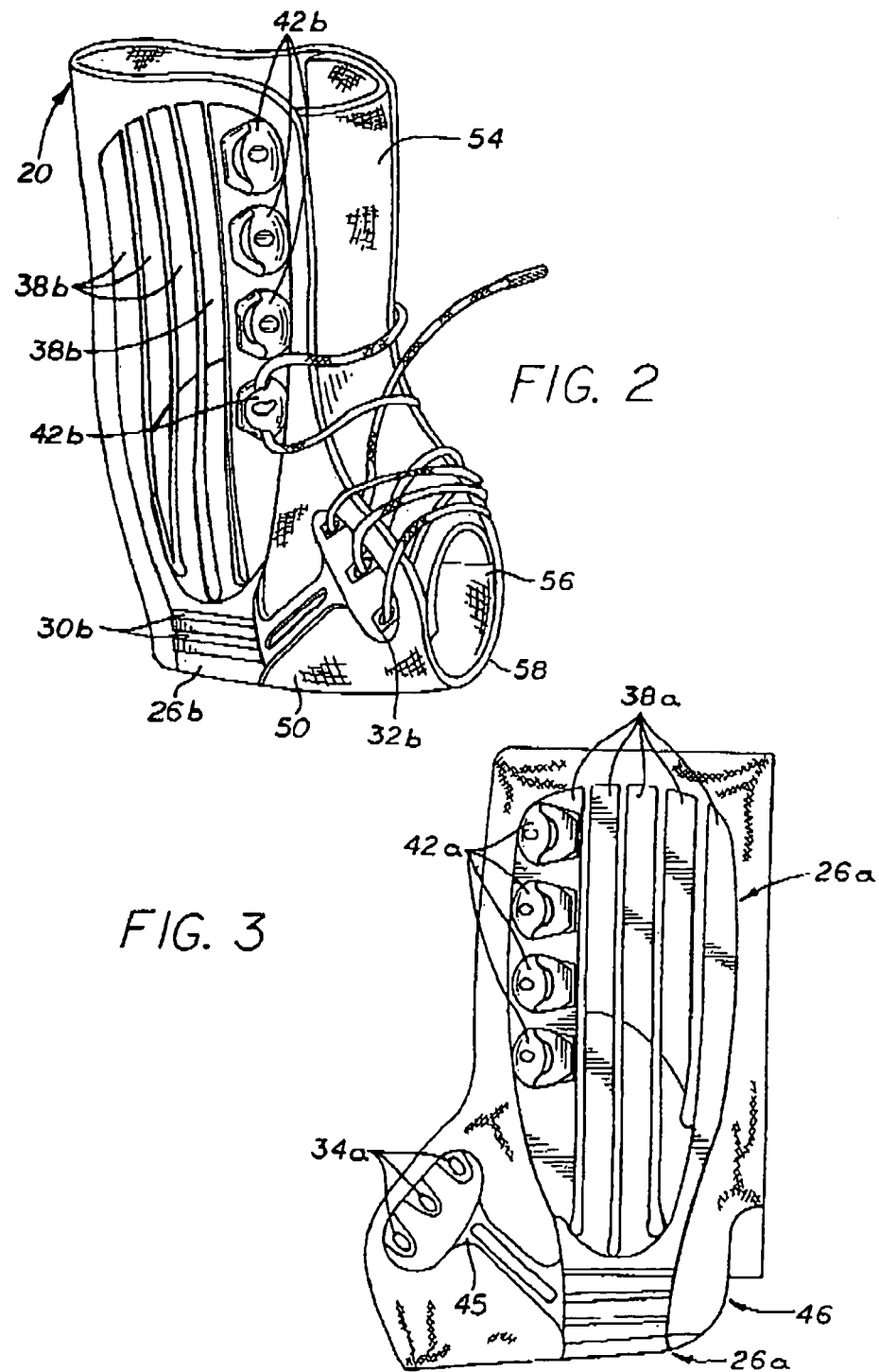

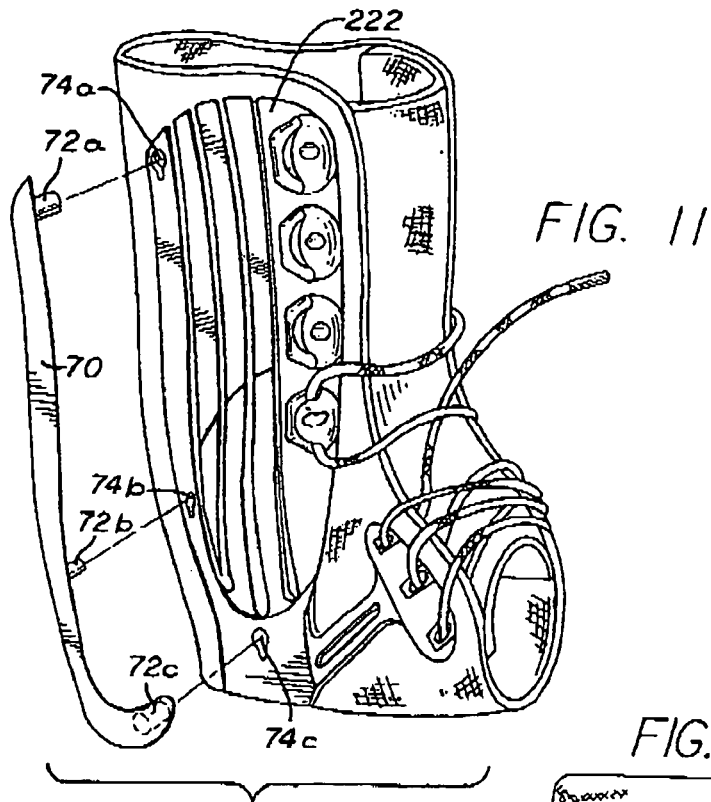
FIG. 11
FIG. 12
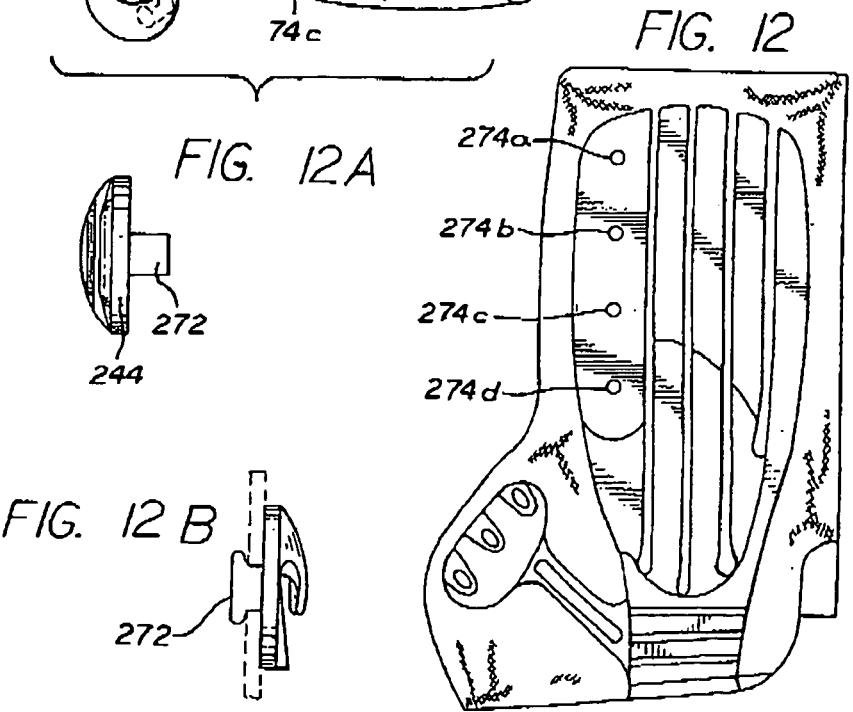
FIG. 12A
FIG. 12B

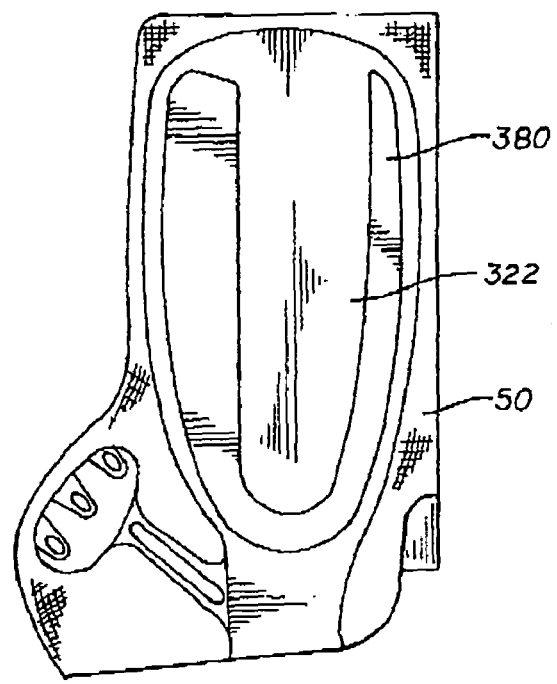
FIG. 13
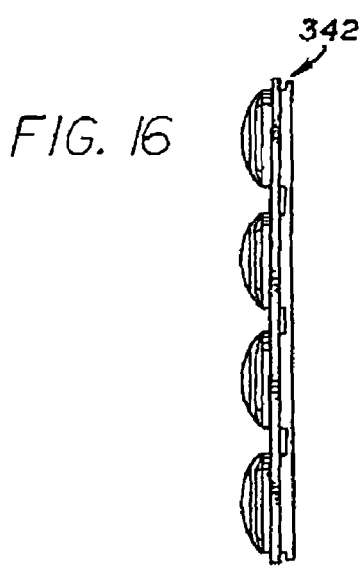
FIG. 16
FIG. 15

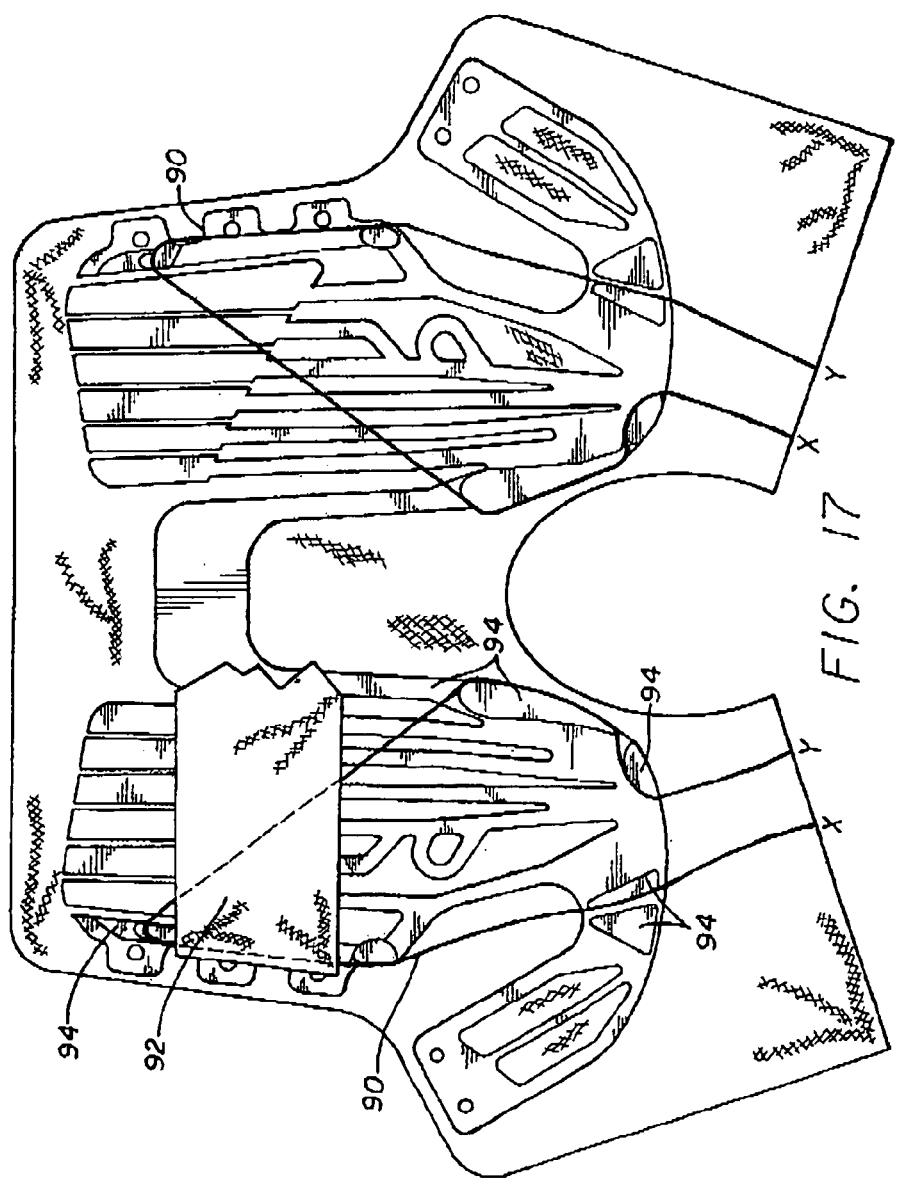

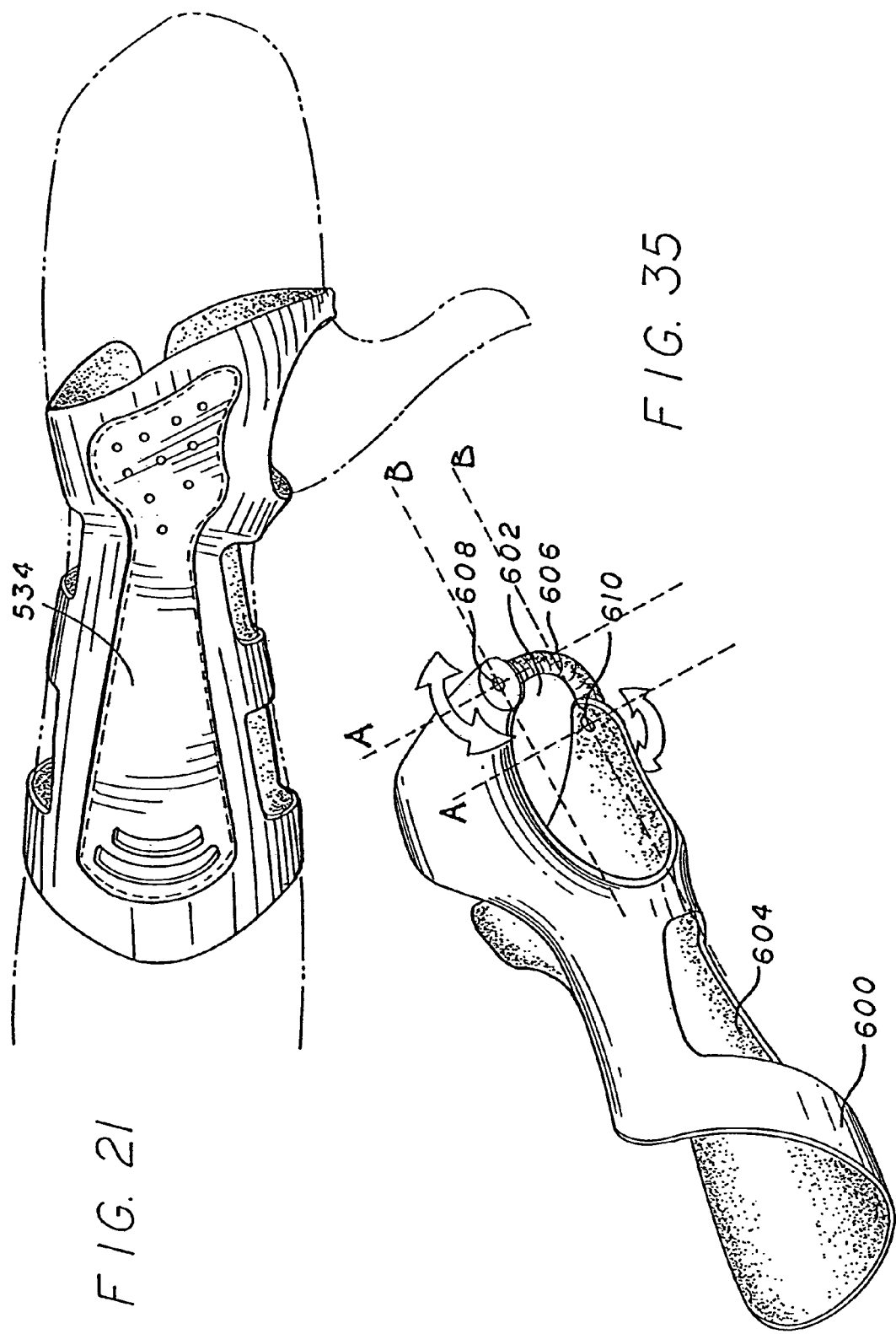

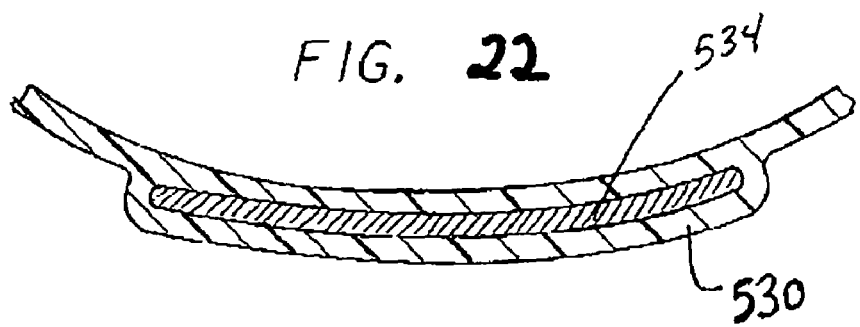
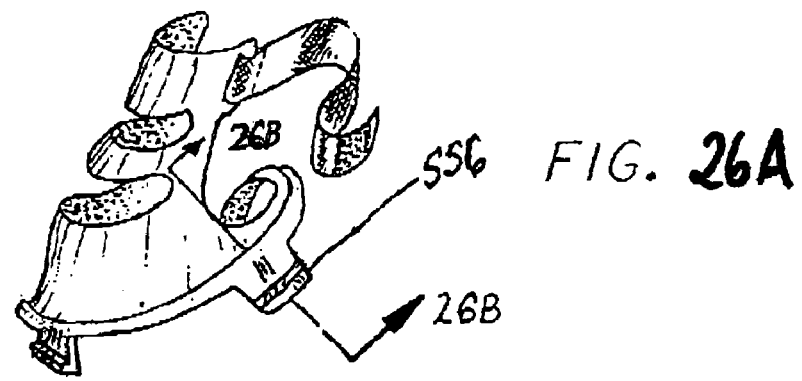
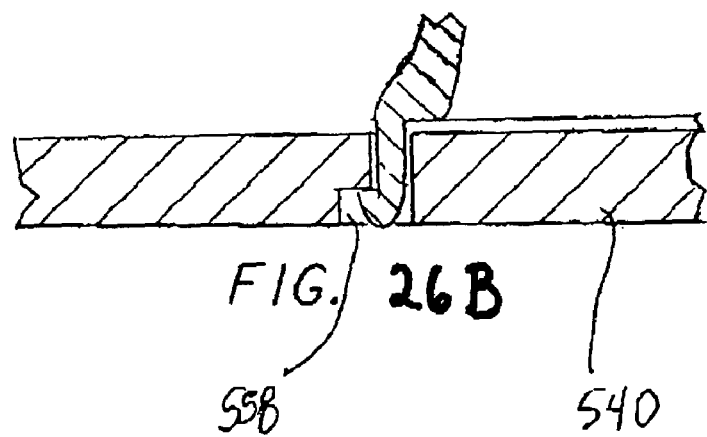

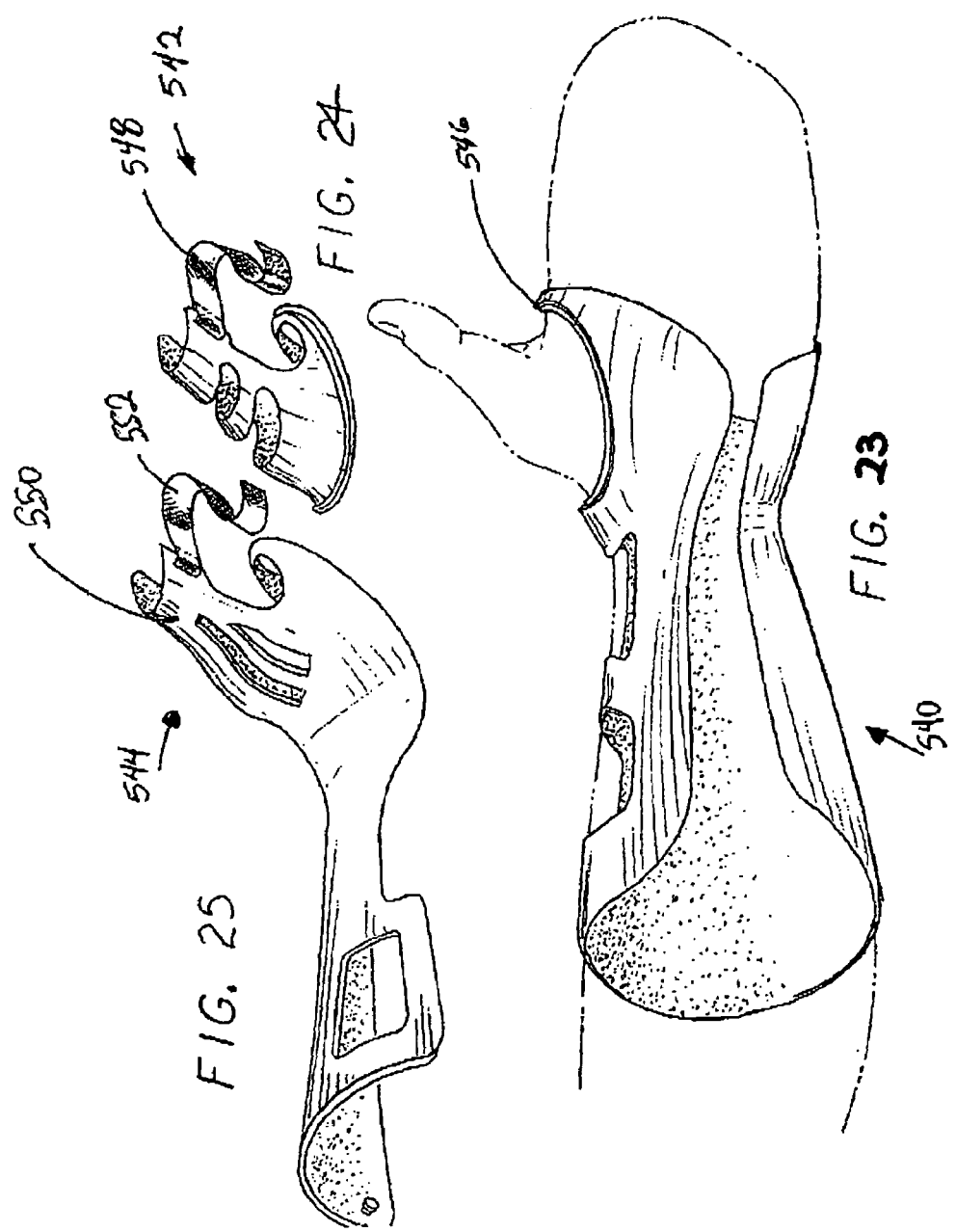

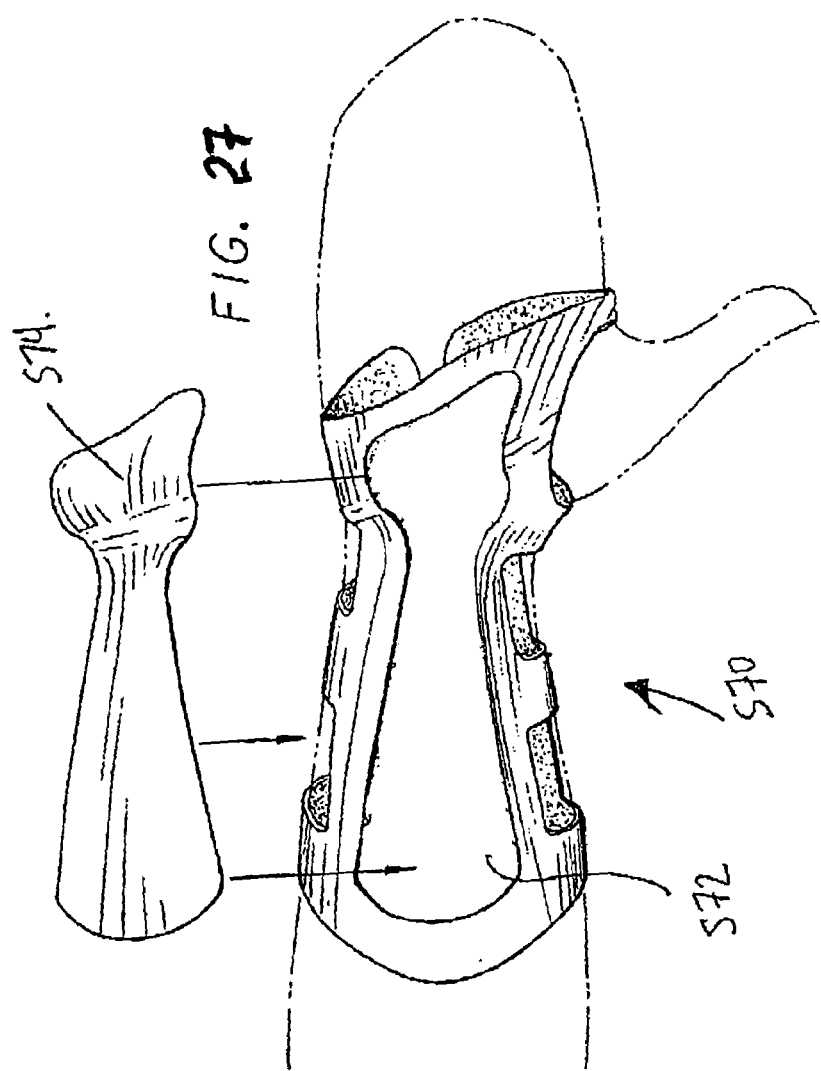

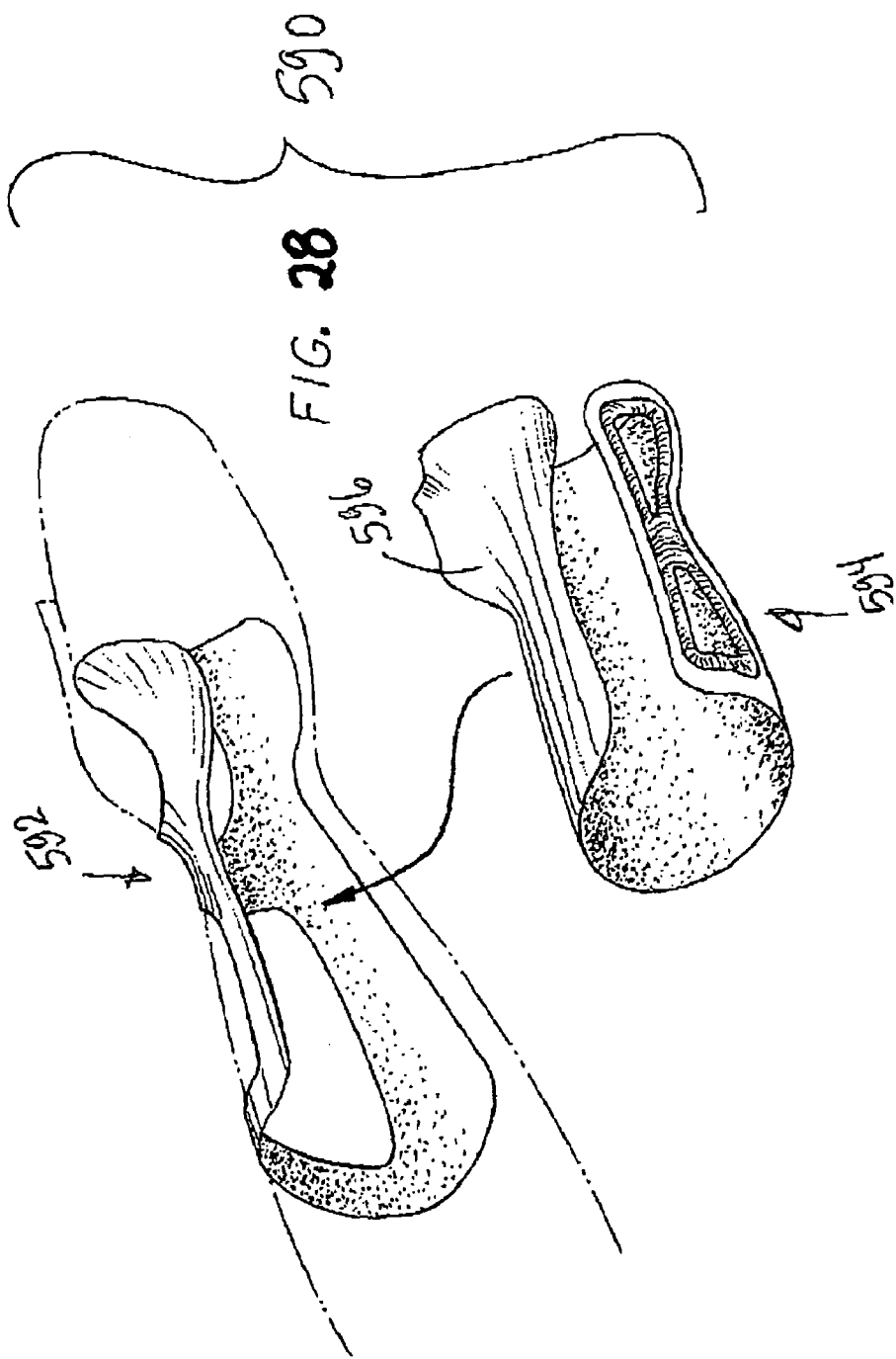

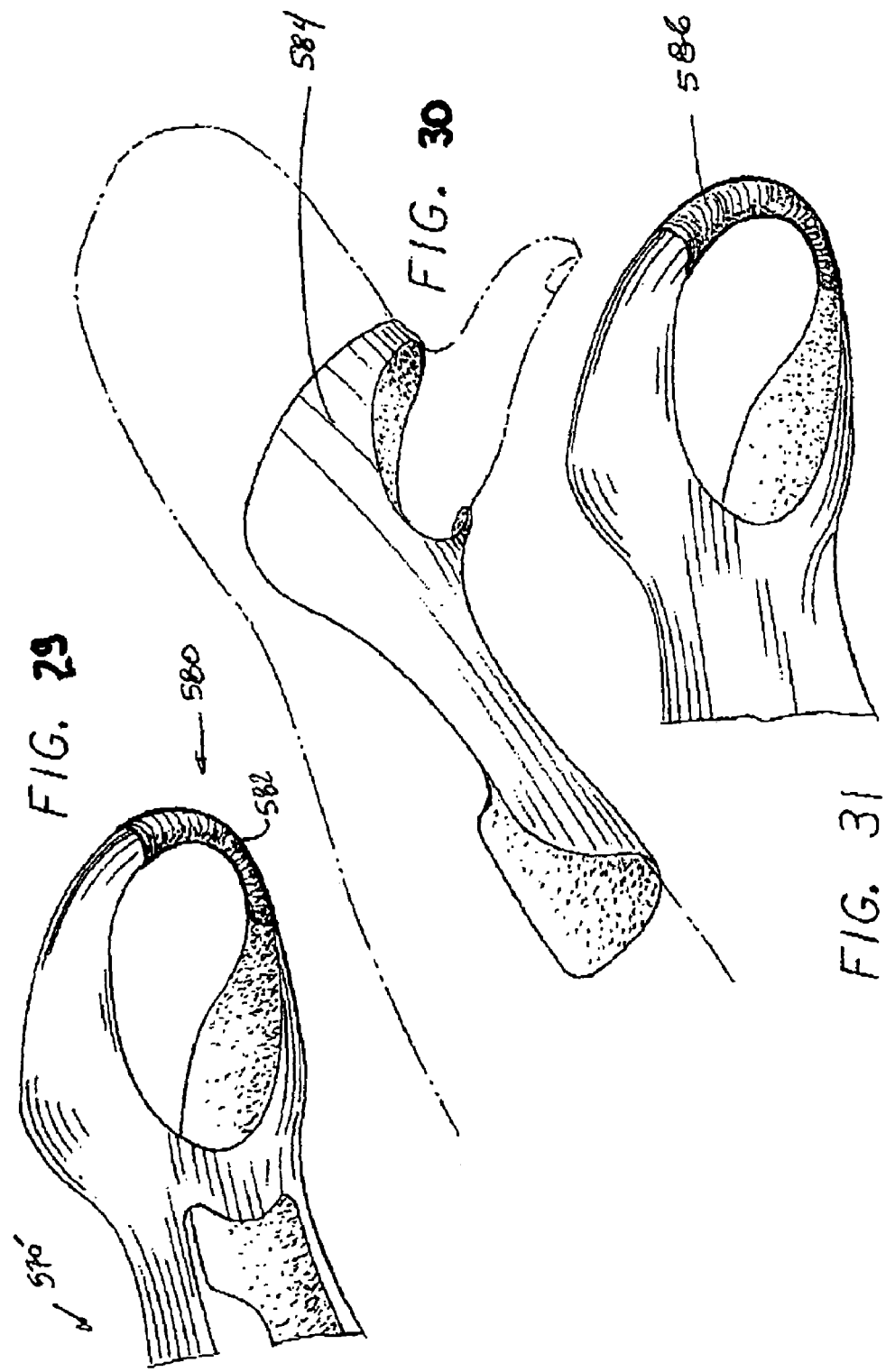

MOLDED ORTHOPAEDIC DEVICES

I. RELATED APPLICATIONS

This application is a continuation-in-part of parent application Ser. No. 09/504,980, filed Feb. 15, 2000, now abandoned, which is a continuation-in-part of Ser. No. 09/018,318, filed Feb. 3, 1998, now U.S. Pat. No. 6,024,712, which is a continuation-in-part of Ser. No. 08/580,129 filed Dec. 28, 1995, now U.S. Pat. No. 5,713,837, all of whose contents are hereby incorporated by reference.

II. BACKGROUND OF THE INVENTION

A. Field of the Invention

The present invention relates to orthopedic supports and, more particularly, to an orthopedic support that has a molded exo-structure.

B. Prior Art

There are a number of known ways to stiffen fabric orthopedic supports for injured parts of the anatomy. U.S. Pat. No. 4,724,847, for example, discloses an ankle brace that has a plurality of pockets. Rigid stay members are inserted into the pockets to form a rigid structure that surrounds and immobilizes the ankle. U.S. Pat. Nos. 3,298,365, 4,280,488, 4,825,856, and 4,440,158, among others, disclose similar arrangements.

A drawback of these designs is that they require a great deal of labor to construct. Workers must be hired to cut many separate pieces of fabric, sew the supports together, insert the rigid stays and so on. A further drawback is that the stays are typically die-cut from plastic of constant thickness. The shape of the stays is therefore quite limited, and the final support often does not fit the anatomy perfectly. While stays can be manufactured to have a particular contour, the manufacturing process is not simple and is often fairly expensive.

Efforts have been made outside of the orthopedic support art to create stiffened, custom-shaped objects by injecting hardenable material into a mold in which fabric has been placed. For example, European Patent Application No. 89103277.3, which the EPO published on Feb. 24, 1989 as publication number 0 332 899, discloses a diaphragm formed by injection molding plastic onto a piece of fabric. The diaphragm acts as a pressure barrier in an automobile engine. European Patent Application No. 87101406.4, published on Feb. 3, 1987 as publication no. 0 234 341, discloses creating fiber reinforced structures for automobiles. Fibrous material is placed into a mold, and then resin is injected into the mold. The resin saturates the fabric and eventually sets, thereby forming a reinforced automobile part. Other examples include U.S. Pat. Nos. 5,093,067 and 5,456,976.

U.S. Pat. No. 5,647,150, which issued Jul. 15, 1997, discloses forming a shoe by stretching a sock about a mold. A thermoplastic film layer is positioned between the mold and the fabric layer. Thermoplastic material is then allowed to flow through the fabric and bond with the thermoplastic film layer, thereby securing the thermoplastic material to the fabric. However, the method requires that the thermoplastic material flow entirely through the fabric in order to bond with the thermoplastic film layer on the opposite side of the fabric. The end result is a shoe with plastic on both the outside and the inside, and the shoe provides no cushioning between the molded plastic and the foot.

U.S. Pat. No. 6,024,712, which issued on Feb. 15, 2000 and which is incorporated by reference herein, presents a number of injection-molded orthopaedic supports. The '712 patent introduces the concept of a molded support having a structural member that may optionally added to the support after the support has already been molded. In particular, FIG. 11 of the '712 patent illustrates an ankle support having an additional frame member that may be optionally secured to the exostructure when further stiffening is required. It is desirable to further extend this concept of easily adapting an already-molded exostructure to the needs of a particular user.

III. SUMMARY OF THE INVENTION

The object of the present invention is to advance the art with respect to orthopedic supports and to provide an improved method for manufacturing orthopedic supports.

Generally speaking, the present invention is an orthopedic support having a flexible inner member and a molded exo-skeleton.

One aspect of the invention relates to a wrist support having a thumb spica. The wrist support includes a molded plastic exostructure supplying support for resisting motion of said wrist. An inner fabric support is attached to said molded exostructure for providing cushioning to the wrist area. A separate, attachable thumb spica member is provided for optionally configuring the wrist support to include a thumb spica. The wrist support has one mode in which the support has no thumb spica, and a second mode in which the support has a thumb spica.

In alternative embodiments, the thumb spica member is attached to said support in the second mode by a method selected from the group constituting ultrasonic welding, snaps, hook-and-loop material, rivets or an adhesive. The thumb spica member may comprise a thumb retention strap, which may include hook-and-loop material. It may also comprise a molded outer exostructure and a softgoods lining in said exostructure.

In one alternative embodiment, the plastic exostructure comprises a forearm portion and a thumb portion. The thumb spica member comprises a thumb supporting structure and a stay portion that attaches to the forearm portion of said exostructure. In other embodiments, the plastic exostructure includes a web-receiving area and a thumb aperture. The thumb spica member is adapted to attach to the plastic exostructure about the thumb aperture.

Another aspect of the invention relates to an orthopaedic support having an attachable stay. A versatile wrist support comprises a molded plastic exostructure supplying support for resisting motion of said wrist. An inner fabric support is attached to said molded exostructure for providing cushioning to the wrist area. A separate, attachable stay for optional attachment to said molded exostructure is provided to add further rigidity to the exostructure. The wrist support has a first relatively flexible mode in which the attachable stay is not attached to the wrist support, and a second relatively stiff mode in which the attachable stay is attached to the wrist support.

In particular embodiments, the stay may be formed from the group of materials constituting aluminum, steel and molded plastic. The stay may be a bendable aluminum stay. The support may also have a third mode in which said aluminum stay has been bent after attachment to the support in order to alter the shape of the support. The support may include a molded recess for receiving said stay.

Another aspect of the present invention relates to a support having a portion that extends across and supports the web of the hand. The support may comprise a molded plastic exostructure supplying support for resisting motion of said wrist. Said molded plastic exostructure may comprise a web portion that is adapted to extend across the web of a hand. A padded, flexible member extends about at least a portion of said web portion to provide cushioning for the web of the hand. The molded plastic exostructure may optionally include a molded recessed area for receiving said padded member.

Another aspect of the invention is an adjustable wrist support having an adjustable forearm portion that can accommodate various sizes of forearms. One such embodiment includes a molded plastic exostructure supplying support for resisting motion of said wrist. An inner cushion is attached to said molded exostructure for providing cushioning to the wrist area. The exostructure has a forearm portion and a hand portion. The forearm portion includes an adjustable closure, wherein the forearm portion may be adjusted to fit the forearms of a variety of different users.

In various embodiments, the adjustable closure comprises a strap having hook-and-loop material. The adjustable closure may comprise a first and second strap, said first strap having a plurality of posts and said second strap having a plurality of holes to receive said posts. The adjustable closure may alternatively comprise a strap secured to said exostructure and a clip adjustably secured to said strap, said clip having an aperture, said exostructure having a hook to which said clip secures.

Another aspect of the invention relates to a method of molding the exostructure onto a central core. One embodiment of the method includes providing a mold comprising a first exterior portion having a first cavity portion, a second exterior portion having a second cavity portion, and a core piece. The mold is then closed such that the core piece is situated within said first and second cavity portions. Plastic is then injected into the mold to form an exostructure of an orthopaedic support about said core piece. The mold is then opened and the core piece is removed with the plastic exostructure formed thereabout. The method may also include removing the plastic exostructure from off of said core and securing padding to the interior of said exostructure, to provide cushioning to the portion of the anatomy.

Another aspect of the present invention relates to a wrist brace having a space to accommodate the web of the hand. A molded plastic exostructure supplies support for resisting motion of said wrist. The exostructure includes a rounded web portion that is adapted to extend across the web of a hand. The rounded web portion has a thumb opening. The brace may optionally include a padded, flexible member extending about at least a portion of the web portion to provide cushioning for the web of the hand. The molded plastic exostructure may include a molded recessed area for receiving said padded member.

It is noted that the present invention encompasses a wide variety of different orthopaedic supports, including splints, such as volar or dorsal splints. The splints may be unitarily molded, and may include a thumbhole and a portion for extending across the web of the hand.

Another aspect of the present invention is a support having an injection-molded exostructure and interior padding. The interior padding is provided with a support structure that is molded onto the padding. The support structure may be bonded to the exostructure to form a padded orthopaedic support. In one embodiment of the invention, the support structure of the interior padding member is attached to said exostructure by a method selected from the group constituting ultrasonic welding, snaps, hook-and-loop material, rivets or an adhesive.

In various embodiments of the present invention, the thickness of the exo-support may be increased or decreased in certain areas, to provide different levels of support and flexibility at different points on the support. The exo-structure may be adapted to receive a separate support member after molding. Also, the exo-structure may be molded over a stay or other member that is attached to the flexible material or otherwise introduced into the mold prior to injection molding.

The support may further comprise straps about which the exo-structure is injection molded, thereby attaching the straps to the support. The support may include one or more bladders, and may also include a pump for inflating the bladders. Alternatively, the support may include gel or foam pads.

The exo-structure may be molded from more than one type of material. For example, the exo-structure may be a more flexible material in one region where flexibility is desired, and a stiffer material in another region where greater stiffness is desired.

Other objects and features of the invention will become apparent from a review of the Detailed Description below, from the drawings, and from the claims.

IV. BRIEF DESCRIPTION OF THE DRAWINGS

FIG. 2 is a side view of the ankle brace of FIG. 1;

FIG. 3 illustrates a sheet of fabric onto which a plastic exo-structure has been injection molded, from which the embodiment of FIG. 1 is constructed;

FIG. 11 is a perspective view of an ankle brace having a removable stay so that the user can vary the stiffness of the brace;

FIG. 12 is a side view of a further embodiment in which the speed laces are attached after the exo-structure has been injection molded onto the fabric;

FIGS. 12A and 12B are embodiments of speed laces that may be used in conjunction with the embodiment of FIG. 12;

FIG. 13 is a side view of a further embodiment in which the exo-structure is molded over a stay member;

FIGS. 15 and 16 are top and side views, respectively, of a speed lace assembly that may be used in conjunction with FIG. 14;

FIG. 17 is an embodiment having a cable support system;

FIG. 21 illustrates a brace formed from the molded exo-structure of FIG. 20;

FIG. 22 is a cross-sectional view taken about line 22-22 of FIG. 21;

FIG. 23 is an illustration of a configurable embodiment of a molded brace;

FIGS. 24 and 25 are components that can be added onto the brace of FIG. 23 in order to form a thumb support;

FIGS. 26A and 26B illustrate an arrangement for snapping the components of FIGS. 24 and 25 unto the base brace of FIG. 23;

FIG. 27 illustrates a further embodiment of a molded brace in which an optional stay can be attached to the brace for further support;

FIG. 28 illustrates a two-part brace in which the soft goods inner liner includes its own plastic shell;

FIG. 29 illustrates an alternative brace in which resilient padding covers an indented portion of the web space bridge portion of the braces;

FIG. 30 is a further embodiment of a molded wrist support;

FIG. 31 illustrates the embodiment of FIG. 30 with additional padding arranged in the web area of the thumb support;

FIG. 35 illustrates an embodiment of a brace having a pivoting bridge for extending across the web portion of the hand;

V. DETAILED DESCRIPTION OF THE PREFERRED EMBODIMENT

Figure 1:
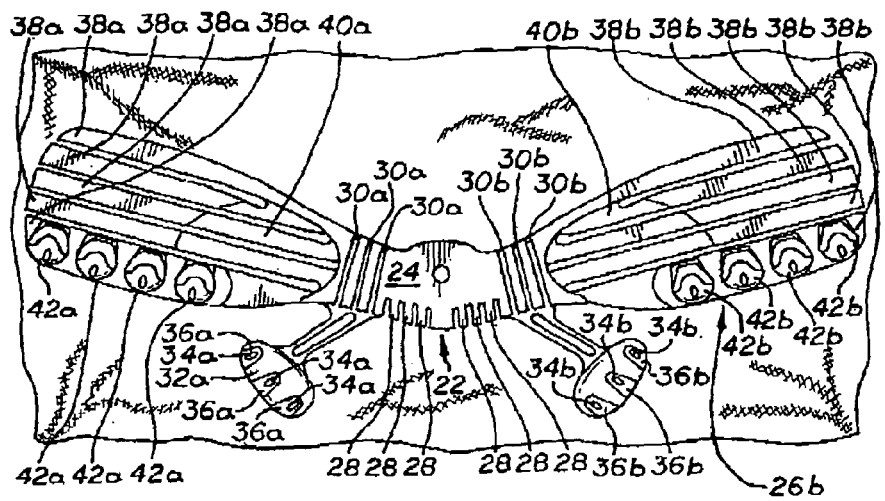
FIG. 1 is a perspective view of one embodiment of an ankle brace as it appears part way through the manufacturing process, according to the present invention.

FIG. 1 illustrates a sheet of flexible porous sheet material 20 onto which a semi-rigid plastic exo-structure 22 has been injection molded. To form the exo-structure 22, the sheet material 20 is stretched across an injection mold, which is then closed under normal hydraulic pressure. The edges of the sheet material 20 normally extend beyond the cavity of the mold (not shown). Once the mold is hydraulically closed, the injection molding mechanism injects melted plastic into the mold to form the exo-structure 22. The melted plastic permeates the porous sheet material 20 and bonds to the sheet material 20 when it cools. Consequently, no additional securing means is necessary to attach the exo-structure 22 to the sheet material 20.

A variety of different materials may be used for both the sheet material 20 and the injection-molded exo-structure 22. For purposes of illustration but not limitation, the sheet material should be a material that is both suitable for use in an orthopedic support and which will allow the melted resin to permeate into it or through it. For example, the sheet material 20 may be a polypropylene knit material, a polyester knit or a nylon. Certain foam laminates and neoprene may be used in some applications. One material that has been used successfully is a polyester spacer fabric available from Gehring Textiles of New York.

The exo-structure may also be made from a variety of different thermoset and thermoplastic materials. Examples include polyethylenes, polypropylenes, thermoplastic eurethanes, TPE's and vinyls. Nylon or glass-filled nylon may be used in applications where the exo-structure must be stiff.

Further considering FIG. 1, the exo-structure 22 includes a heel portion 24 and two side supports 26a and 26b. The heel portion includes a plurality of cut-outs 28 that allow for conformability and fit. Channels 30a and 30b extend along either side of the heel portion 24. When the manufacturer folds the assembly into a finished ankle brace, such as that which FIG. 2 illustrates, the manufacturer may fold the brace along any of the channels 30a and 30b in order to size the heel.

The exo-structure of FIG. 1 includes two lacing extensions 32a and 32b. The extensions 32a and 32b include a thin portions through which extend a plurality of dorsal lace holes 34a and 34b, respectively. The thin portions extend to the edge of the extensions to provide wells 36a and 36b for a shoe lace.

The side supports 26a and 26b include a plurality of fingers 38a and 38b, respectively. The fingers stiffen the support, yet permit the support to adjust to the shape of the ankle and permit the support to flex somewhat during use. The thickness of the fingers may be varied to alter the performance of the support. In the particular embodiment that FIG. 1 illustrates, the exo-structure has a thin region 40 that makes the support more flexible in an area corresponding to the ankle. The support is then more comfortable, allowing for the brace to conform to the contours of the ankle bones in that area. The fingers 38a and 38b are thicker at the ends, away from the ankle, in order to stiffen the support where less flexibility and more support is desired.

Figure 4:
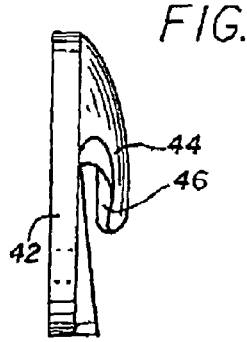
FIG. 4 is a side view of a speed lace of the embodiment of FIG. 1.
Figure 5:
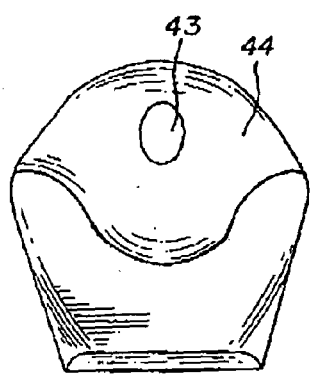
FIG. 5 is a is a top view of the speed lace of FIG. 4.

The exo-structure of FIG. 1 also includes two sets of speed laces 42a and 42b, about which a lace can wrap, as FIG. 2 illustrates. The speed laces 42a and 42b also include lace apertures 43 (FIG. 5), which provide the end-user with the option of either wrapping the shoe lace about the speed laces to lace the support quickly, or running the lace through the lace apertures for very secure lacing. As FIGS. 2 and 4 illustrate, each speed lace has a portion 44 that extends up and over the plane of the rest of the exo-structure 22, providing a portion about which the lace may be wrapped. It should be known to those in the injection molding art that a special mechanism may be employed to form the speed laces. In particular, a spring-loaded lifter may be employed in the mold to automatically push a portion of the mold away from the protruding portion of the speed lace when the injection molding machine is opened.

Figure 6:
FIG. 6 is another side view of the speed lace of FIG. 6.

As FIGS. 4 and 6 illustrate, each of the speed laces may include a small rib 46 that provides tension to the lace during lace-up. The tension from the small rib prevents the lace from loosening. The rib acts to pinch the shoe lace when pulled into place, securing the lace by compression and friction. The width of the opening at the rib is less than the thickness of the lace, such that the lace is secured when pulled underneath the rib.

After the exo-structure 22 has been injection molded onto the sheet 20, the manufacturer can then form the exo-structure 22 and the sheet 20 into a support 48 (FIG. 2). The sheet 20 must first be cut, such as by die cutting, to form the outer body 50 of the support. The sheet 20 can be cut in a variety of different ways. The sheet 20 can be die-cut after the injection molding step. Alternatively, the mold can be designed to cut the sheet during the molding process. The sheet material can be stored on a roll, then fed from the roll to the mold for injection molding. As a further alternative, the sheet 20 can be cut in advance and held in place within the mold by means of hanging and locating pins.

Referring to FIG. 3, a heel opening 46 may be cut into the sheet material 20. The heel opening 46 allows the heel of the user to extend outside of the support, for added comfort and ventilation. A strip of binding material (not shown) may be sewn about the edges of the ankle hole to cover the cut edges and to prevent the edges from tearing. A small semi-circular piece of cushioning material (FIG. 3) may be attached to the inside rim of the heel opening 46. The small piece of cushioning material functions to cushion the top portion of the calcaneus.

Referring again to FIG. 2, a tongue 54 is secured to the support. The tongue 54 is typically made of a comfortable material such as neoprene or another foam, so that the tongue cushions the pressure from the laces. The tongue is typically sewn onto the support, but may be attached in other ways conventional in the art.

The support may include an inner liner 56 made from a flexible, porous material that provides breathability and compression. The inner liner 56 may be a thin sheet of polyester spacer fabric. The inner liner 56 may be sewn onto the support, either directly or in conjunction with a thin strip of binding material 58 at the edge of the support.

Figure 7:
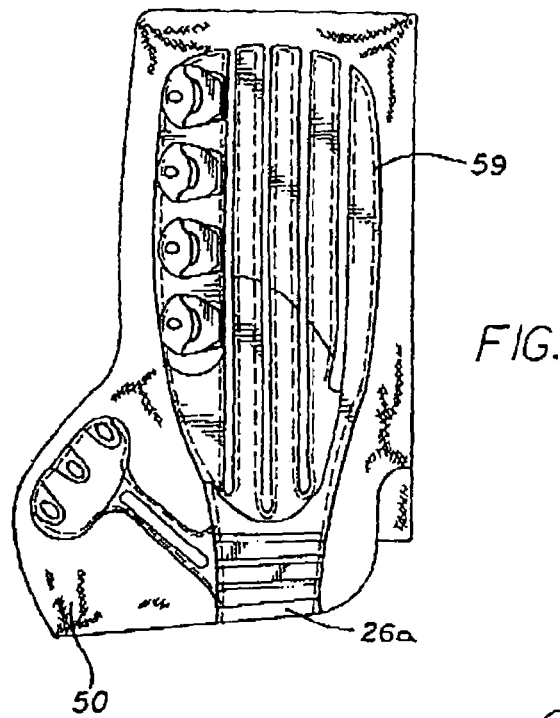
FIG. 7 is a side view of an additional embodiment of an ankle brace in which the exo-structure is both injection molded and sewn onto the fabric for added reinforcement.

FIG. 7 illustrates an alternative embodiment in which the exo-structure 22 is sewn onto the sheet material 20. The exo-structure may be formed separately and then sewn onto the sheet material. Alternatively, the exo-structure 22 may first be injection molded onto the sheet material 20, as described above, then sewn as with sew lines 59 for reinforcement. If the exo-structure is first injection-molded onto the sheet material 20, the sewing serves to reinforce the bond between the exo-structure and the sheet that already exists. As an alternative or a supplement to sewing, various solvent based adhesives can be introduced onto the material prior to injection molding. The adhesive then acts to further bind the exo-structure to the sheet. However, it should be noted that in the presently preferred embodiment, the injection molding process itself binds the exo-structure to the sheet, so that no additional adhesive or sewing is needed to secure the exo-structure to the sheet.

The sets of fingers 38a and 38b of the embodiment of FIG. 2 help conform the support to the shape of the ankle. The fingers allow the support to adapt to a swollen ankle, for example, and to adjust the shape as the swelling goes down. The fingers provide longitudinal support while allowing for compression. The fingers in the embodiment of FIG. 2 get thinner in the region 40 close to the ankle, which is typically tender when the ankle is injured, in order to minimize pressure points. The fingers are thicker away from the ankle in order to provide additional support.

Figure 8:
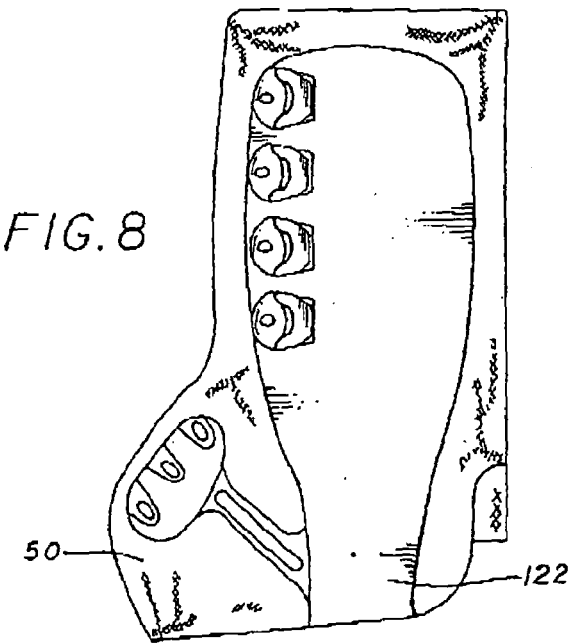
FIG. 8 is a side view of an additional embodiment in which the exo-skeleton does not have the fingers of the embodiment of FIG. 1.

The embodiment of FIG. 8 provides an alternative to the fingers of FIG. 2. The exo-structure 122 is continuous. Rather than having fingers that adapt to the shape of the ankle, the exo-structure 122 is contoured to fit the ankle. As with the embodiment of FIG. 2, the exo-structure 122 of FIG. 8 is formed in standard injection-molding equipment and is injection molded directly onto the underlying flexible sheet material.

Figure 9:
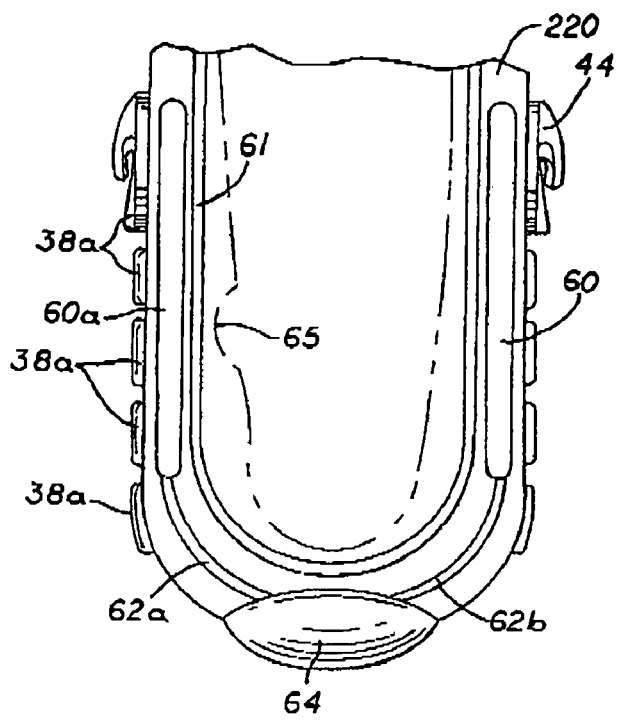
FIG. 9 is a cross-sectional view of an embodiment having a pump and bladders.
Figure 10:
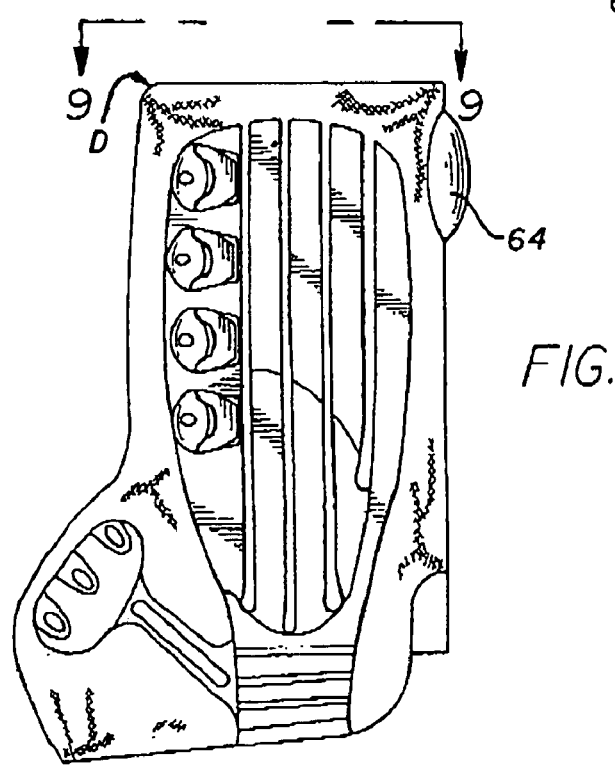
FIG. 10 is a side view of the embodiment of FIG. 9.

Embodiments of the present invention may include one or more bladders. FIGS. 9 and 10 illustrate an embodiment having bladders 60a and 60b embedded in the walls of the support. Bladders embedded in the wall of a support are conventional in the art. However, the embodiment of FIG. 9 also has an injection-molded exo-structure 22 on the outside of the support, which is a feature of the present invention.

The embodiment of FIG. 9 includes the two bladders 60a and 60b, an inner liner 61, and tubes 62a and 62b extending from a respective bladder to a pneumatic bulb pump 64. To inflate the bladders, the user repeatedly presses the bulb pump 64. Each bladder will normally be provided with a valve that prevents air from escaping from the inflated bladder through the tubes 62a and 62b, in order to maintain the inflation of the bladders. The bladders serve to provide additional support to the ankle 65. A conventional release valve is provided in conjunction with each of the bladders to selectively let pressure out of the bladders when they are inflated.

The bladders are normally formed within the sheet material 220 prior to injection-molding the exo-structure onto the sheet material. However, alternative arrangements are possible in which, for example, the bladder and tubing is inserted into the sheet material 220 after the exo-structure has been formed. In many embodiments, the bladders will go in between the sheet material 220 and the inner liner. While the bladders are generally air-filled, they may be filled with foam instead of, or in addition to, air under pressure.

As an alternative to the air bladders of FIG. 9, the support may be provided with gel pads. The walls of the support may be provided with pouches into which the gel pads are inserted after the injection molding has already been completed. The gel pads either would be placed next to the skin, between the ankle and the inner liner, or would be sandwiched between the outer layer 220 and the inner liner. With this arrangement, the support may be used for hot/cold therapy, in which hot and/or cold gel packs are inserted into the support.

In some applications it may be desired to further stiffen the exo-structure. Consequently, the embodiment of FIG. 11 is designed to permit the user to selectively add and remove an additional frame member 70. The frame member 70 has posts 72a, b and c which may be inserted into compatible apertures 74a, b, c to removably secure the frame member 70 to the exo-structure. The presently preferred frame member 70 is injection-molded plastic, although the frame member could be made from a wide variety of materials, including metals for extra stiffness.

The concept of adding structural members that FIG. 11 illustrates can be extended beyond merely adding an additional frame member 70. Other structural components, such as pads, stays, electronic devices and any other attachment suitable for attachment to an orthopedic support may be attached to the exo-structure and/or the flexible sheet material.

For example, the speed laces may be formed separately and attached after the exo-structure has been injection molded. FIG. 12 illustrates such an arrangement, with attachable speed laces 244 (FIG. 12A) each having a post 272 to insert into a mating aperture, such as apertures 274a-d. An alternative post 272' may be employed, in which the post includes a knob 276 that allows the speed lace 244' to snap into the exo-structure. By attaching them to the exo-structure separately, the speed laces may be made from a different material than the exo-structure. For example, the speed laces may be formed of a harder, more durable material than the exo-structure, which might be made of a more flexible material. In addition to snapping into place as FIG. 12B illustrates, the speed laces may be attached by other known means, such as sonic welding or riveting.

Another embodiment of the present invention involves over-molding an exo-skeletal semi-rigid plastic framework over a more rigid plastic material. The more rigid plastic piece is either pre-injection molded or die-cut and then placed into the mold along with the fabric material. The more rigid plastic piece may also be pre-injection molded onto the fabric material. The exo-skeletal material may then be formed of a softer material for better comfort, with the more rigid plastic material providing the rigidity. The exo-skeletal material is injection molded over the more rigid plastic material and onto the fabric.

Referring to the embodiment of FIG. 13, the exo-skeletal semi-rigid plastic framework 322 is molded over a plastic stay member 380 that is made of a more rigid plastic or metal material. The stay member 380 can be pre-injection molded by itself or onto the flexible sheet material 20. In either case, both the stay member 380 and the fabric sheet are placed (separately or pre-attached attached) together in the injection mold. The exo-structure 322 is then injection molded onto the sheet and over the stay member 380.

Figure 14:
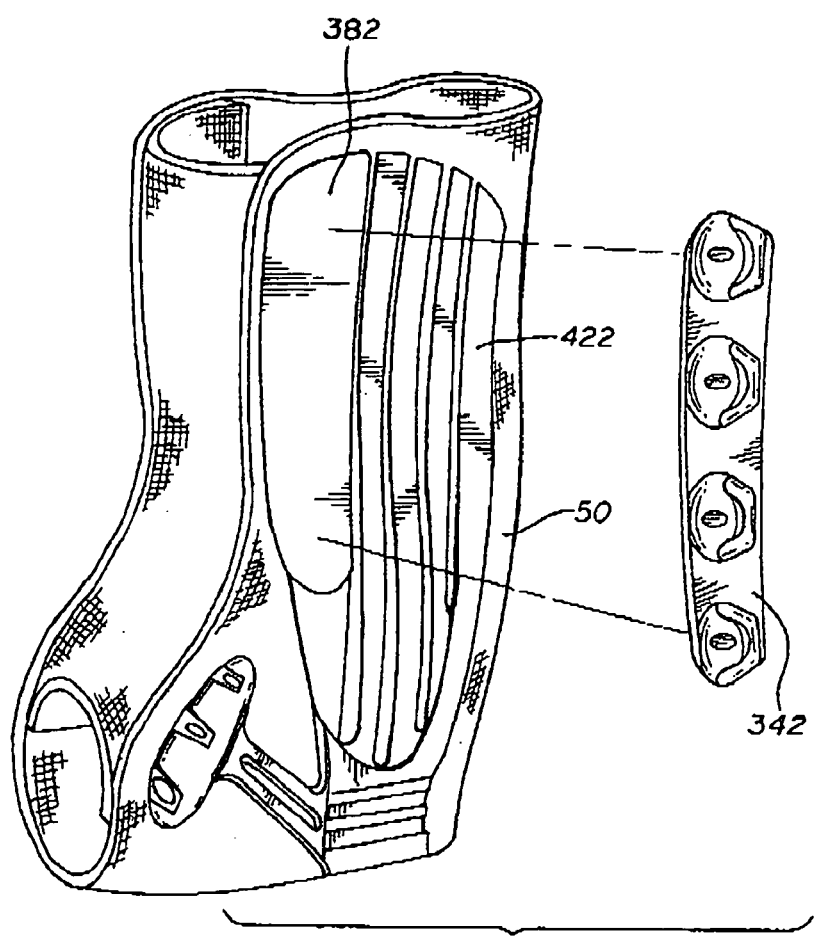
FIG. 14 is a further embodiment in which the speed laces are provided in a separate assembly.

This concept can be extended to molding an exo-structure about a pre-fabricated speed lace assembly. The speed laces may be molded with a thin base of plastic (FIGS. 14, 15 and 16). The speed lace assembly 342 is then placed in the injection mold along with the flexible sheet material The exo-structure plastic is then injection molded on to the fabric and over the speed lace assembly, thereby bonding the speed lace assembly in place. Alternatively, the speed lace assembly may be attached at a predetermined area 382 after the exo-structure 422 is formed, by means of welding, an adhesive, and/or other attachment means known in the art. (FIG. 14).

The foregoing has described a presently preferred embodiment of the invention, as well as alternative embodiments. However, it should be understood that the scope of the invention is not limited to what is described in the Detailed Description. Numerous variations may be employed within the scope of the invention. For example, as illustrated in FIG. 17, an orthopedic support according to the present invention may include a cable reinforcement system over the exo-skeletal framework to provide additional medial/lateral support and compression. The cable 90 may be a single filament line, for example, that interacts with the lacing and/or strapping system. When the laces or straps are tightened they pull the single filament wire 90 taut. For example, in FIG. 17, a strap 92 pulls the wire 90 taut when tightened. A system of guides 94 may be molded as part of the exo-structure, and the cable 90 may pass through the guides.

The support may be fitted with various attachments and hardware. For example, the exo-structure may be molded to include pins, channels, grooves, pockets and the like in which attachments such as stays, stiffeners, pipes, electronic and/or magnetic devices, gel pads, heaters, coolers, medicine delivery mechanisms, and a variety of other devices may be mounted. In certain applications, electric wiring and/or electronic devices may be added into the mold prior to molding, with the exo-structure being injection molded over or around the electric and/or electronic devices.

Similarly, the orthopedic support may be modified for use in particular climates, such as by adding insulating pads and/or layers to the support for use in cold weather. The heel portion may also be closed rather than open in particular applications. Apertures may be cut into the sheet material for added ventilation in hot weather.

Hook and loop material may be added to the support to replace or supplement the laces, and various other changes may be made. within the scope of the invention. In another embodiment, straps are permanently attached during the injection molding process. The straps are placed in the injection mold with the porous sheet material. When the exo-skeletal framework is injection molded onto the sheet material, the straps are permanently molded into place. In some embodiments, three-dimensional shapes may be introduced into the mold to form three-dimensional finished products, such as certain thumb braces, wrist, and other braces having complex shape. As yet another alternative, the exo-structure may be formed on the interior side of the support rather than on the exterior, then covered with a soft liner before applying the support to the injured portion of the anatomy. The present invention can also extend to applications beyond orthopedic supports, such as devices for horses and other animals and protective pads for athletes.

The preferred method of manufacturing most embodiments of the present invention is with injection molding, in which a thermoplastic or thermoset material is heated and then injected into a mold. However, other approaches may be used as well. For example, an exo-structure may be formed onto a flexible sheet by placing the sheet across or into a mold, then closing the mold, then pouring a liquid resin that is at room temperature (or slightly heated) into the mold and allowing the resin to dry onto and to bond to the flexible sheet material to form the exo-structure.

The exo-structure is normally injection molded onto the flexible sheet material. However, instead of injection molding the exo-structure onto the flexible material, the exo-structure may be removably attached to the underlying flexible material with Velcro, snaps, and/or other conventional attachment means. The flexible underlying material may also be provided with pockets, slits or the like into which the exo-structure may be inserted and which will removably hold the exo-structure in place on the support.

The drawings illustrate various means for holding the support member and cushioning material to the portion of the anatomy to be supported. Such means are not limited to what is illustrated in the drawings however, as the support member and cushioning material can be held to the portion of the anatomy with straps, laces, and any other means that is conventional in the ankle brace art.

Figure 18:
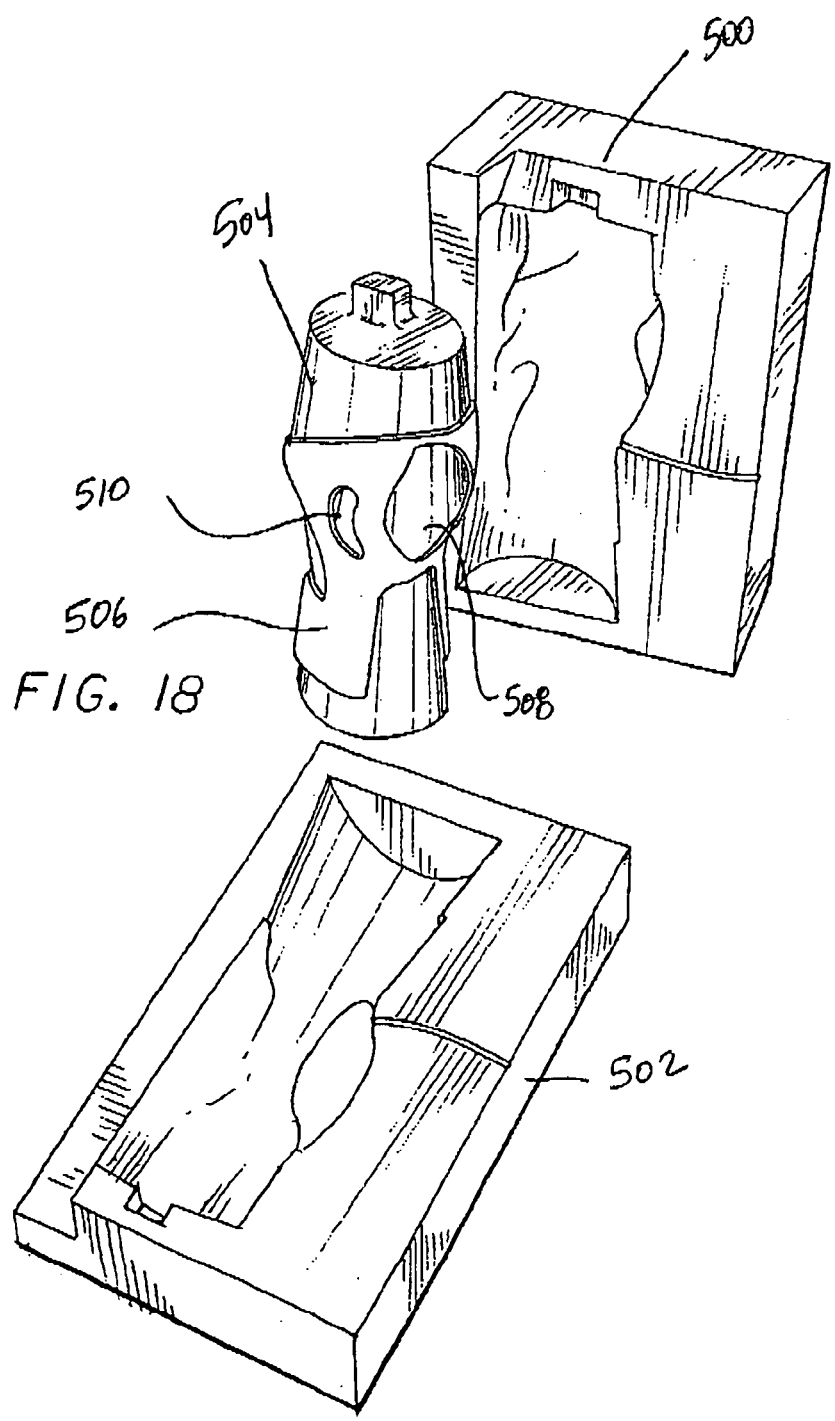
FIG. 18 is a further alternative embodiment, in which the exo-structure is molded in a three-dimensional shape inside of a mold.

FIG. 18 illustrates an apparatus for forming an injection molded wrist brace. The wrist brace may optionally have an incorporated stay and a unitarily molded web capturing area. The brace may incorporate thick and thin areas in different portions of the brace, in order to provide additional support in some areas and greater flexibility in other areas. The method of manufacturing the brace includes molding an exo-structure about a three-dimensional core, rather than molding the plastic onto a relatively flat piece of material and then folding it up into a brace.

In one embodiment of a method of manufacturing such a brace, a stockinet or tubular soft good padding member is extended about the three-dimensional core. Plastic is then molded about the core and into the soft good material, to form a unitary, padded support. In an alternative method of manufacturing the brace, the exo-structure is molded first about the three-dimensional mold core. The soft good padding is then attached separately to the wrist-shaped molded exo-structure. Considering FIG. 18 in some detail, a mold includes a first mold piece 500, a second mold piece 502 and a mold core 504. In FIG. 18, an exo-structure 506 has been molded about the mold core 504. The molded exo-structure includes a thumb hole 508 and an optional aperture 510 for relieving pressure in a particular portion of the wrist.

Figure 19:
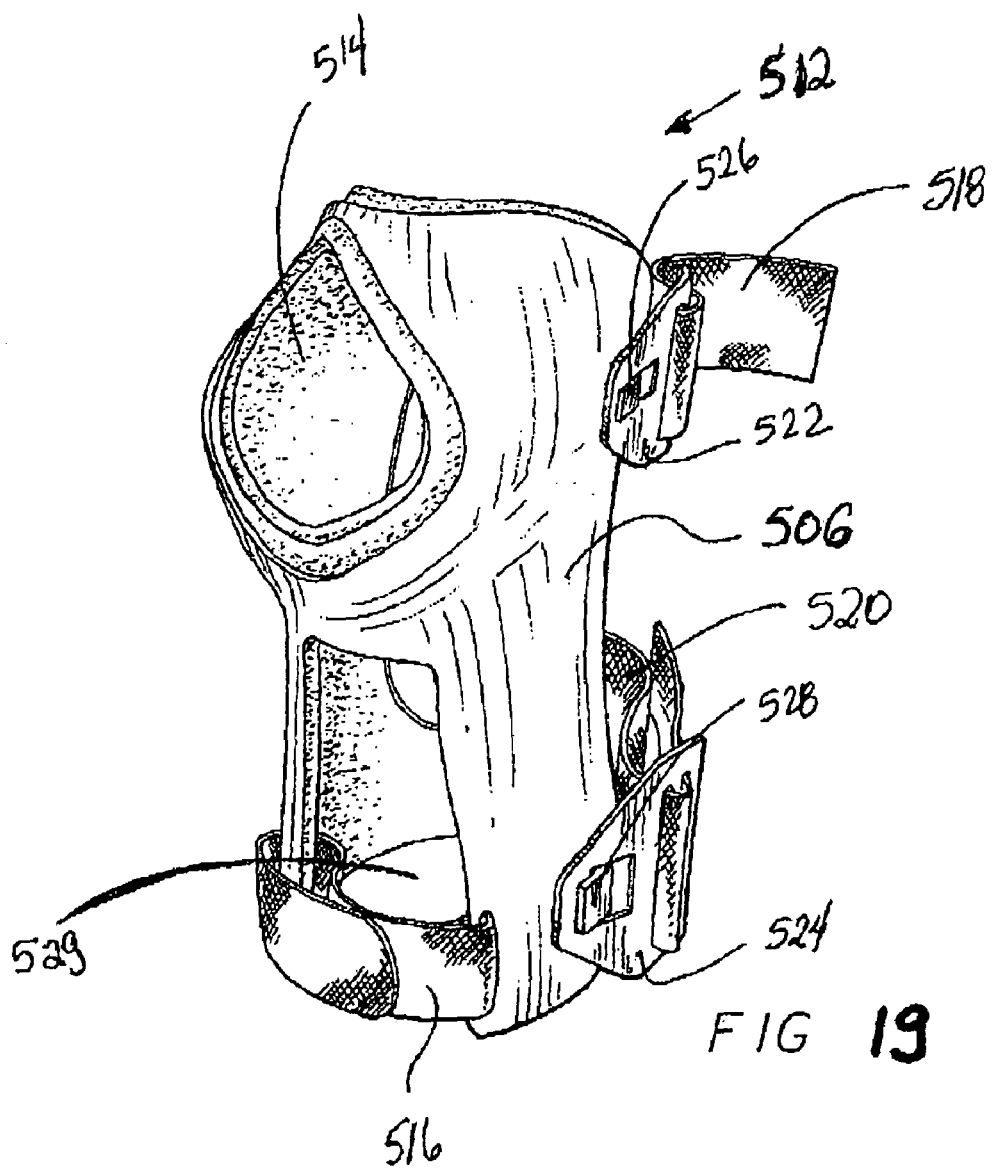
FIG. 19 illustrates a finished orthopaedic support incorporating the molded exo-structure of FIG. 18.

FIG. 19 illustrates the exo-structure 506 as it appears on a finished wrist support 512. A soft padding interior has been attached to the exo-structure 506. The soft padding interior 514 is attached to the exo-structure 506 after the exo-structure 506 has been molded. The soft padding 514 can be attached to the exo-structure 506 with an adhesive, such as a heat-activated or urethane-based adhesive, or by other known attachment means, such as rivets, hook and loop type fasteners, or even molded directly to the exo-structure. The pad may also be attached using other heating means, and may even be formed at the same time it is bonded to the exostructure.

A radial forearm adjustment strap 516 includes hook and loop type material so that the forearm portion of the brace may be adjusted on the user. This adjustment strap 516 is a mechanism that permits the manufacturer to make a smaller number of different sized braces to fit the wide range of different sized users. Experience has shown that the diameter of the forearm can vary greatly among different people, even between people who have approximately the same sized hands. By making the forearm portion of the brace adjustable in size, one brace can be made to fit a wide variety of users.

FIG. 19 also illustrates additional closure straps 518 and 520 for further securing the brace to the wrist and forearm. Each of straps 518 and 520 include respective clasps 522 and 524. The clasps hook onto hooks 526 and 528, respectively, to secure the support to the wrist and forearm.

Another feature of FIG. 19 is an opening 529 in which there is no material. The purpose of the opening 529 is to provide pressure relief in the region of the arm often associated with carpal tunnel syndrome. The pressure relief opening 529 prevents pressure that could result if that portion of the arm swelled against the material of the brace. The pressure relief opening 529 facilitates recovery from carpal tunnel syndrome, and may also help to prevent the occurrence of carpal tunnel syndrome. In alternative embodiments, the pressure relief opening 529 may be filled in with a mesh or other relatively flexible material, yet still provide pressure relief.

Figure 20:
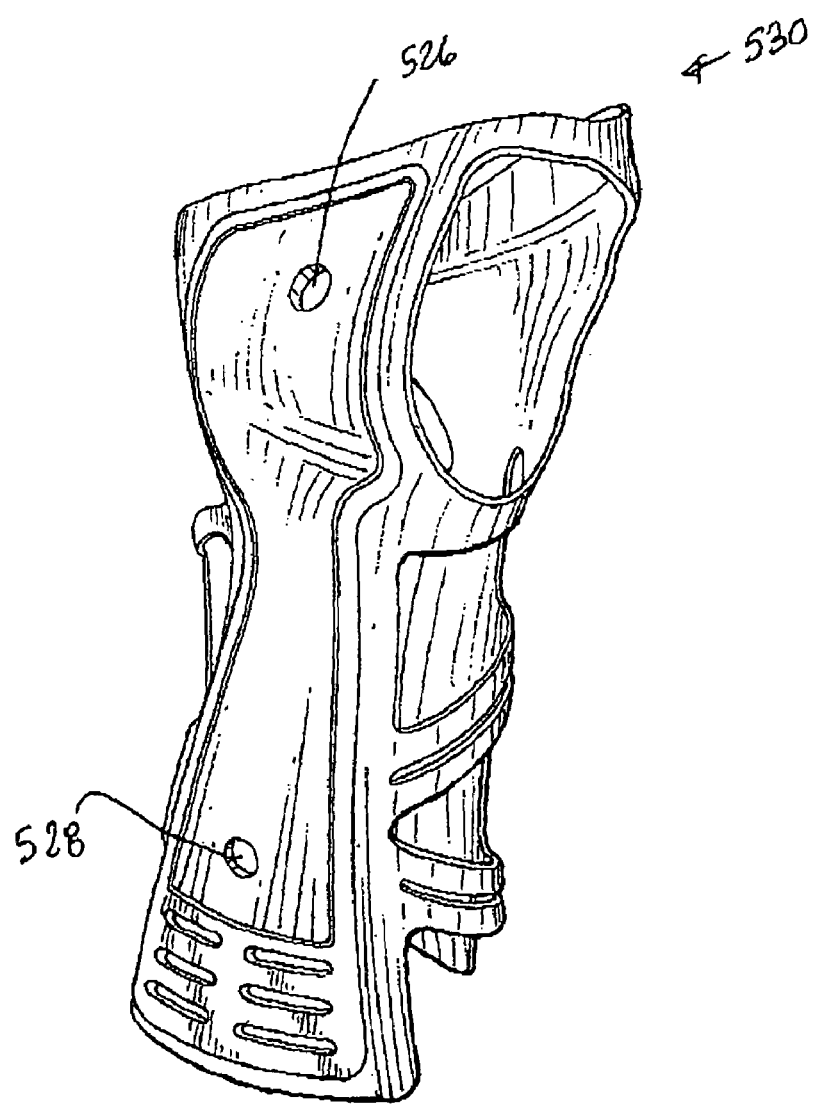
FIG. 20 illustrates a further alternative embodiment of a molded exo-structure.

FIG. 20 illustrates another molded embodiment of the present invention. In particular, FIG. 20 illustrates the molded exo-structure 530 of the embodiment. FIG. 21 illustrates the exo-structure of FIG. 20 having been completed into an orthopedic wrist support. In this embodiment, an aluminum stay 534 is molded into the exo-structure itself. The aluminum stay provides support for the forearm and wrist structure, and typically permits a doctor or other user to bend the support somewhat to customize the shape of the support for a particular user. To manufacture the support of FIG. 21, a thin contoured aluminum stay is placed in a mold arrangement similar to that illustrated in FIG. 18. The stay is held in place by pins within the mold (not shown), which explains the apertures 536 and 538 in FIG. 20. As can be appreciated by those skilled in the art, the aluminum stay 534 can alternatively be made of other materials, such as steel. Other materials may be used, depending on the desired stiffness or flexibility of the support. Various types of stays, such as palmer and dorsal stays, may be incorporated.

FIG. 22 is a sectional view taken about section 22-22 in FIG. 21. FIG. 22 illustrates the aluminum stay 534 embedded within a portion of the molded exo-structure 530.

FIG. 23 illustrates a further alternative embodiment in which a brace 540 may be further configured with optional additional components, such as those illustrated in FIGS. 24 and 25. FIG. 24 illustrates a thumb splint 542 that can be optionally attached to the brace 540 at thumb hole 546. The thumb splint 542 includes a strap 548 for securing the thumb within the splint. The strap 548 may have an end portion with hook and loop type material, and a mating piece of hook and loop material may be adhered to the side of the thumb splint 542, at which the strap 548 may attach.

If the user desires greater support and reinforcement for the orthopedic support 540, a member 544 such as that shown in FIG. 25 may be coupled to the support 540. The component 544 includes a thumb support splint 550, and a support strap 552 for securing the thumb within the stint. Either of splint 542 or 544 may be attached to support 540 by way of adhesive, ultrasonic bonding, rivets, snaps, or other means known in the art for securing member to one another. An advantage of the arrangement illustrated in FIGS. 23 through 25 is that a single support 540 may serve as the base for a number of different embodiments of a wrist support.

FIGS. 26A and 26B shows that the component 542 may be snapped into place in one embodiment of the system of FIGS. 23 through 25. In the embodiment of FIG. 26A, the thumb splint 542 is provided with snaps such as 556. The snap hook members such as 556 engage with apertures such as 558 in FIG. 26B to enable the splint 542 to snap into place on the brace 540 in FIG. 23.

FIG. 27 illustrates a further embodiment of an orthopedic wrist support 570 having an indentation 572 to receive an optional stay 574. The brace can be used without the optional stay 574, but the stay 574 may be added to the brace to further stiffen the brace, when desired. The stay 574 may be made of any of a variety of materials, such as aluminum, steel or a molded polymer. When thin aluminum or other metals are used, the doctor or end-user may bend stay 574 to alter the shape of the support for custom fitting. A molded polymer stay, however, is less expensive and may be equally effective for stiffening the support in specific circumstances.

FIG. 28 illustrates a two-part support 590, which includes an exterior exo-structure 592 and a padded soft goods member 594. The padded soft goods member 594 may have a molded exo-structure of its own 596. The function of the exo-structure 596 is to provide additional support to the wrist along the ulnar side, while not circumferentially surrounding the hand with plastic to do so. The entire unit 594 is manufactured separately from member 592 and then is attached by means of ultrasonic bonding, adhesive, snaps, hook and loop material fasteners, rivets or other fastening means known in the art.

FIG. 29 illustrates the portion 580 of the support 570 that extends across the web area between the thumb and the forefinger. This portion 580 may be referred to as a web portion bridge, because it extends across the web portion of the hand. In this particular embodiment, a soft over-mold 582 is molded onto the portion 580 to provide padding for the web area of the hand. The advantage of the over-mold 582 is that there is no hard plastic to dig into the web area of the hand. The molded polymer portion of the support retains the shape of the web area 580, while the over-mold provides the cushioning. As a result, the web area 580 does not stretch or otherwise become misshapen.

FIG. 30 illustrates an alternative embodiment of the brace in which less material is used on the upper and lower portions of the wrist, and a greater quantity of material is used along the side of the wrist. Although means for support are not illustrated in FIG. 30, the various other means illustrated in other Figures may be used, such as hook and loop material fasteners, straps, snap-straps, and various other means. FIG. 31 illustrates a concept similar to that shown in FIG. 29, wherein a soft over-mold is placed in the web area of the support. The embodiment of FIG. 31 has an indentation such that when the soft good over-mold is formed over the indentation, the over-mold is flush with the rest of the molded brace, or the difference in thickness is at least reduced.

Figures 32, 33:
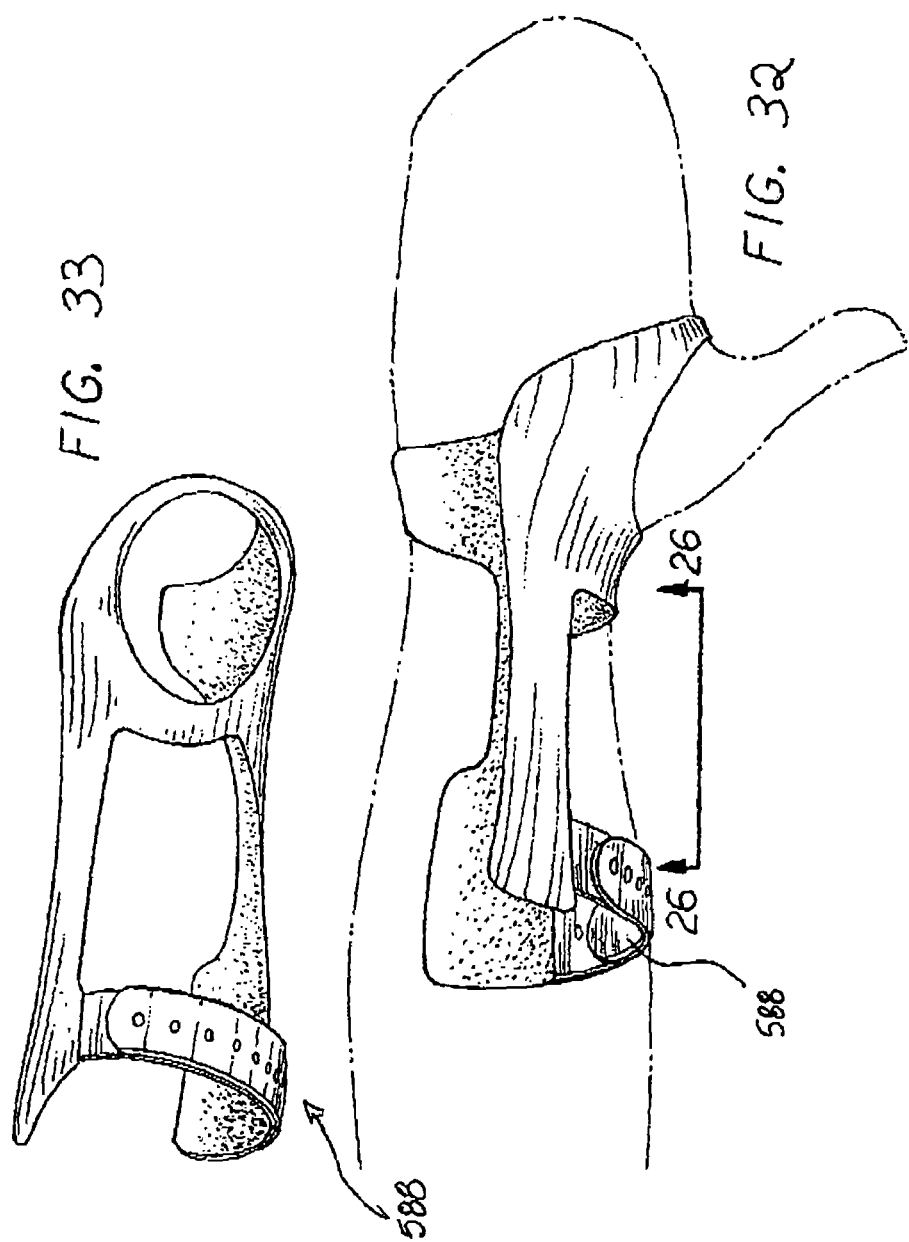
FIGS. 32 and 33 illustrate an alternative attachment arrangement in which an adjustable baseball cap type securing system is utilized.

FIGS. 32 and 33 illustrate a further embodiment of means for adjusting the forearm portion of the support. This particular means for adjusting the forearm portion of the brace 588 is similar to baseball cap-style adjustment means, which allow the user to expand or contract the distance between two members. The adjustment mechanism consists of a first member having a plurality of spaced posts, and a mating member having a plurality of apertures with openings sized such that the posts may pass through the openings under pressure from the user, but will not withdraw from the apertures without significant pressure. This type of fastening mechanism is widely known and is used extensively on baseball caps.

Figure 34:
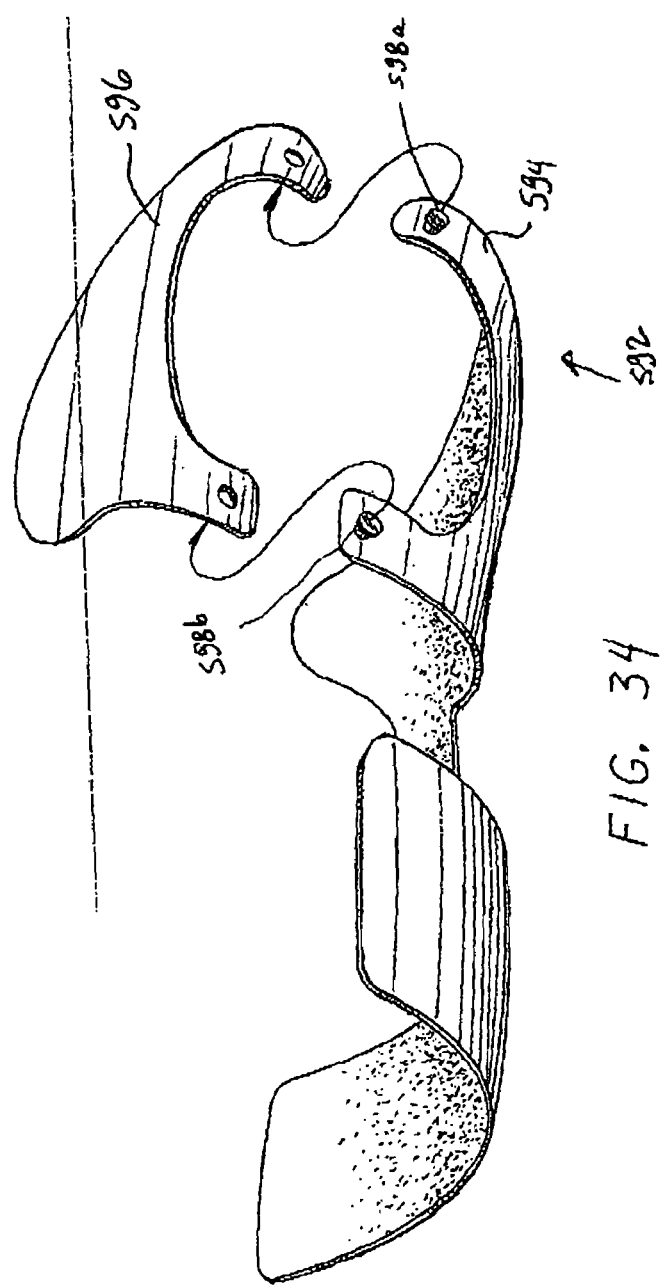
FIG. 34 illustrates a further alternative embodiment having a molded exo-structure that is formed in separate parts and then is joined together after molding.

FIG. 34 illustrates an embodiment 592 of a wrist support having a first piece 594 and a second mating piece 596. Unlike other embodiments in which the entire support is formed in a single molding step, the embodiment 592 of FIG. 34 can be formed in separate pieces in separate molding steps. After molding is completed, the pieces 594 and 596 are joined together by way of snaps 598A and 598B or by alternative joining means such as ultrasonic bonding, adhesives, rivets, or other means known in the art. Although FIG. 34 illustrates an embodiment of the brace 592 in which there are just two members that are joined together to form the completed brace, alternative embodiments may be made of multiple additional components that are formed separately and then joined together after molding. The embodiment of 592 may be supplemented with padding, additional supports, or other components to stiffen, strengthen or otherwise improve the function of the brace. The embodiment of FIG. 34 also allows for construction of a variety of different braces using, for example, a standard piece 594 and a selection of different pieces 596. The piece 596 may be chosen from the selection of different pieces to construct a support having characteristics or configuration that is desired.

FIG. 35 illustrates a further embodiment of a support that has an exostructure 600 with a thumbhole 602 and padding 604. A web bridge 606 is provided to extend across the web portion of the hand. In this embodiment, the web bridge is pivotally mounted at hinge points 608 and 610, so that the web bridge can pivot as the web of the hand moves back and forth relative to the web bridge. The axes of rotation about which hinge points 608 and 610 rotate are represented by dashed axes lines A. Dashed lines B represent planes generally defining the surface area of the exostructure 60 near the hinge points 608, 610. The rotation of the hinge points 608 and 610 is about axes lines A which are not co-planar with the planes defined by dashed lines B. The hinge points 608 and 610 can be any of a variety of different mechanical hinges known in the art.

Embodiments of the wrist brace may have a thumbhole, with an overmold about the thumbhole. The overmold may be of a softer, more resilient material than the exostructure itself, to help cushion the thumb from the exostructure. Similarly, overmolds may be applied about other openings in the wrist brace or on other types of supports for various purposes. In embodiments having a portion extending across the bridge of the hand, the portion extending across the bridge may be an overmolded material.

Embodiments of the present invention may include overmolding in certain areas to provide a non-skid surface. For example, in wrist support embodiments, the wrist support may have a palm section with an overmold on at least a portion of the palm section. The overmold provides a non-skid surface, to reduce the tendency of the palm portion from sliding on surfaces such as a table top or other surfaces on which the palm may come into contact.

In another variation, in embodiments in which a support is supplemented with a padding member that has its own plastic shell, the padding member does not necessarily need to be bonded to the exostructure, but may be attached in some other way, such as by rivets, hooks, hook-and-loop material, snaps or other attachment methods known in the art. The plastic structure that is molded onto the padding may serve to provide support to the anatomy that the exostructure does not otherwise provide.

Figure 36:
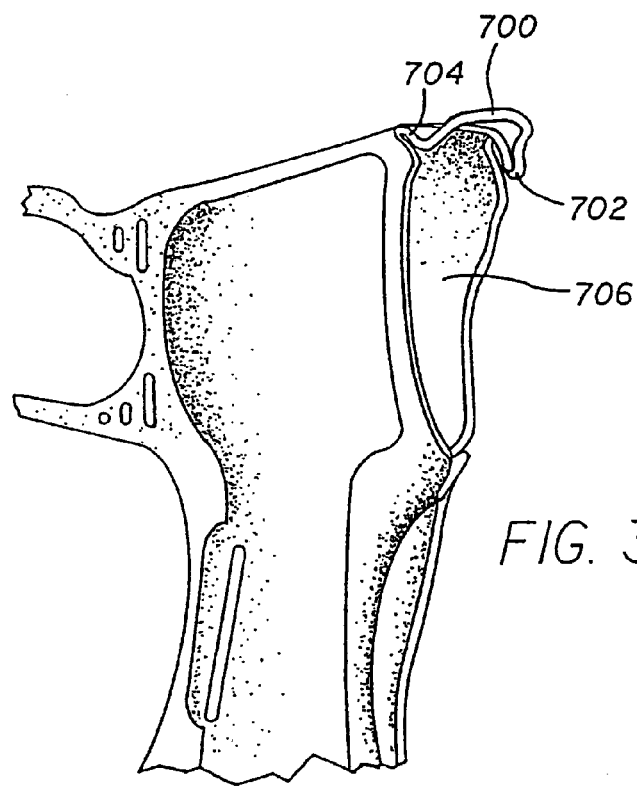
FIG. 36 illustrates the use of generally "S"-shaped junctions where the web bridge portion of a wrist support connects at either end with the adjacent support pieces.
Figure 37:
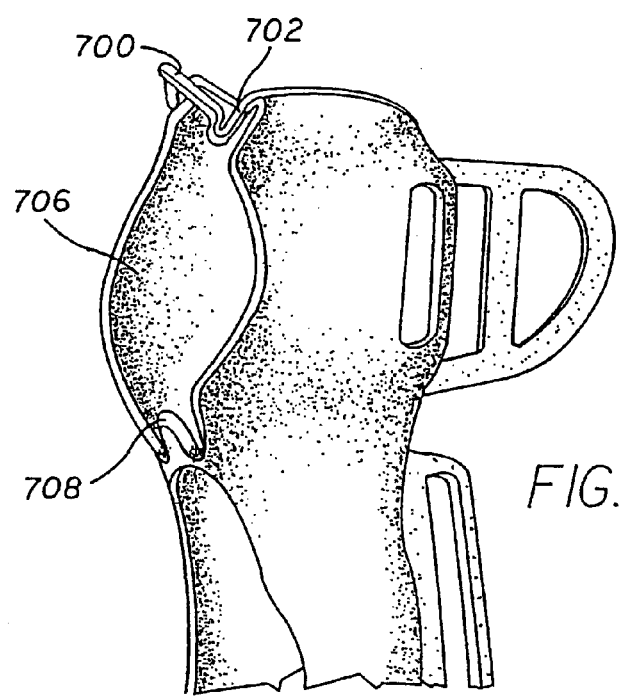
FIG. 37 illustrates the use of generally "S"-shaped junctions at the bottom of the thumb opening of the brace.

It is also possible to provide a support according to the present invention with arrangements to provide additional flexibility in specific areas. For example, FIGS. 36 and 37 illustrate how specific portions of the support may be provided with indented areas to increase flexibility. In FIG. 36, a portion 700 to extend across the bridge of the hand is joined at either end by indented, "S"-shaped junctions 702 and 704, respectively. The junctions and the portion 700 are unitarily molded with the adjoining portions of the brace. The generally "S"-shaped junctions allow the portion 700 to flex easily. In FIG. 36, reference numeral 706 refers to the thumb opening in the brace. The indented areas 702, 704 may have an "S" shape, or other indented shape. Areas of the support in which this arrangement may be used to advantage include the portion of the support in which a web bridge meets the body of the brace, as well as in the thenar bridge, which is the area across the base of the thumb FIG. 37 illustrates one such "S" shaped junction at the bottom of the thumb opening 706. The indented areas can be covered with an overmold, to provide particularly comfortable areas on the support.

In another wrist brace embodiment of the invention, a molded plastic exostructure may be covered with an overmold on at least any edges where digital motion of the hand causes the skin to contact the edges of the exostructure. The overmold provides comfort to the user.

Accordingly, the present invention is not limited precisely to the arrangements as shown in the drawings and as described in detail hereinabove.

What is claimed is:

1. A versatile wrist support comprising:
   a molded plastic exostructure supplying support for resisting motion of said wrist;
   said molded plastic exostructure comprising a hinged web portion that is adapted to extend across the web of a hand wherein an axis of rotation of said hinge is not co-planar with said molded plastic exostructure; and
   a padded, flexible member extending about at least a portion of said web portion to provide cushioning for the web of the hand, wherein said web portion includes fabric onto which plastic has been molded.

2. A versatile wrist support as defined in claim 1, wherein said molded plastic exostructure includes a molded recessed area for receiving said padded member.

3. A versatile wrist support as defined in claim 2, wherein the support has a thumb aperture and comprises an overmold about the thumb aperture.

4. A versatile wrist support as defined in claim 1, wherein the thickness of said exostructure is non-uniform to provide different levels of support at different points on the support.

5. A versatile wrist support as defined in claim 1, wherein said molded plastic exostructure comprises first and second separate pieces.

6. A versatile wrist support as defined in claim 5, wherein said first and second separate pieces are attached to one another by a method selected from the group constituting ultrasonic welding, snaps, hook-and-loop material, rivets or an adhesive.

7. A versatile wrist support as defined in claim 1, wherein the wrist support has a palm portion, with an overmold on at least part of the palm portion.

8. A versatile wrist support as defined in claim 1, wherein said padded flexible member is attached to said exostructure by a method selected from the group constituting ultrasonic welding, a snap, hook-and-loop material, a hook, a rivet, and an adhesive.

9. A versatile wrist support as defined in claim 1, wherein the support has a carpal tunnel pressure relief opening.

10. A versatile wrist support as defined in claim 1 further comprising a thumb spica for mounting to said wrist support for providing additional support for the thumb.

11. A versatile wrist support as defined in claim 1 further comprising a stay for mounting on said exostructure to provide additional support.

12. A versatile wrist support as defined in claim 1 further comprising straps for holding the support onto the user.

13. A versatile wrist support as defined in claim 1 wherein said exostructure is of non-uniform thickness.

14. A versatile wrist support comprising:
a molded plastic exostructure supplying support for resisting motion of said wrist;
said molded plastic exostructure comprising a hinged web portion that is adapted to extend across the web of a hand wherein an axis of rotation of said hinge is not co-planar with said molded plastic exostructure; and
a padded, flexible member extending about at least a portion of said web portion to provide cushioning for the web of the hand, wherein said exo-structure comprises plastics of different densities.

15. A versatile wrist support comprising:
a molded plastic exostructure supplying support for resisting motion of said wrist;
said molded plastic exostructure comprising a hinged web portion that is adapted to extend across the web of a hand wherein an axis of rotation of said hinge is not co-planar with said molded plastic exostructure; and
a padded, flexible member extending about at least a portion of said web portion to provide cushioning for the web of the hand, wherein an inner fabric support is attached to the molded exostructure by directly molding the exostructure onto the inner fabric support in a single molding operation without use of an adhesive or a fastener.

16. A wrist support comprising:
a molded plastic exostructure supplying support for resisting motion of said wrist;
said molded plastic exostructure comprising an ergonomically contoured web portion that is hinged and adapted to extend across the web of a hand, said contoured web portion partially defining a thumb opening wherein an axis of rotation of said hinge is not co-planar with said molded plastic exostructure.

17. A wrist support comprising as defined in claim 16 further comprising a padded, flexible member extending about at least a portion of said web portion to provide cushioning for the web of the hand.

18. A wrist support as defined in claim 16, wherein said molded plastic exostructure includes a molded recessed area for receiving said padded member.

19. A versatile wrist support as defined in claim 16, wherein said exostructure comprises plastics of different densities.

20. A versatile wrist support as defined in claim 16, wherein the thickness of said exostructure is non-uniform to provide different levels of support at different points on the support.

21. A versatile wrist support as defined in claim 16, wherein said molded plastic exostructure comprises first and second separate pieces.

22. A versatile wrist support as defined in claim 16, wherein said first and second separate pieces are attached to one another by a method selected from the group constituting ultrasonic welding, snaps, hook-and-loop material, rivets or an adhesive.

23. A wrist support as defined in claim 16 wherein said support is a volar splint.

24. A wrist support as defined in claim 16 wherein said support is a dorsal splint.

25. A versatile wrist support comprising:
a molded plastic exostructure supplying support for resisting motion of said wrist;
said molded plastic exostructure comprising a hinged web portion that is adapted to extend across the web of a hand, wherein an axis of rotation of said hinge is not co-planar with said molded plastic exostructure; and
said web portion comprising a flexible fabric that has been molded/secured into place on the exostructure.

26. A wrist support comprising:
a molded plastic exostructure supplying support for resisting motion of said wrist;
said molded plastic exostructure having edges which contact the skin of a user's hand during digital motion;
a soft and flexible web portion attached by a hinge to said molded plastic exostructure wherein an axis of said hinge is not co-planar with the molded plastic exostructure; and
a softer plastic molded over said edges to increase comfort.

* * * * *